(12) United States Patent
Luciano

(10) Patent No.: US 9,141,764 B2
(45) Date of Patent: Sep. 22, 2015

(54) SYSTEM AND METHOD FOR ONLINE INTEGRATED MULTIPLE TABLET ORDERING

(75) Inventor: Robert A. Luciano, Reno, NV (US)

(73) Assignee: EDGE MEDICAL PROPERTIES, LLC, Reno, NV (US)

( * ) Notice: Subject to any disclaimer, the term of this patent is extended or adjusted under 35 U.S.C. 154(b) by 432 days.

(21) Appl. No.: 12/945,709

(22) Filed: Nov. 12, 2010

(65) Prior Publication Data

US 2012/0123907 A1    May 17, 2012

(51) Int. Cl.
  *G06Q 30/00* (2012.01)
  *G06F 19/00* (2011.01)
  *G06Q 30/06* (2012.01)
  *G06Q 50/22* (2012.01)

(52) U.S. Cl.
  CPC ........ *G06F 19/3462* (2013.01); *G06F 19/3456* (2013.01); *G06Q 30/0601* (2013.01); *G06Q 30/0633* (2013.01); *G06Q 30/0641* (2013.01); *G06Q 50/22* (2013.01)

(58) Field of Classification Search
  CPC ............... G06Q 30/06–30/0643; G06Q 50/22; G06Q 50/24; G07F 17/0092; G07F 19/3462; G07F 19/3456; Y10S 283/90
  USPC .................................... 705/1.1–4, 26.1–27.2
  See application file for complete search history.

(56) References Cited

U.S. PATENT DOCUMENTS

| | | | |
|---|---|---|---|
| 2,294,220 A | 8/1942 | Albertson |
| 3,126,129 A | 3/1964 | Weinberg |
| 3,254,828 A | 6/1966 | Lerner |
| 3,308,962 A | 3/1967 | Bryant |
| 3,409,721 A | 11/1968 | Applezweig |
| 3,410,450 A | 11/1968 | Fortenberry |
| 3,432,951 A | 3/1969 | Cherrin |
| 3,497,982 A | 3/1970 | Schulz |
| 3,503,493 A | 3/1970 | Nagy |
| 3,703,955 A | 11/1972 | Inacker |
| 3,780,856 A | 12/1973 | Braverman |
| 3,921,804 A | 11/1975 | Tester |

(Continued)

FOREIGN PATENT DOCUMENTS

| | | |
|---|---|---|
| DE | 3502647 A1 | 7/1986 |
| WO | WO 96/13790 A1 | 5/1996 |

(Continued)

OTHER PUBLICATIONS www.walgreens.com Dated from Jun. 10, 2007-Sep. 19, 2010. [recovered from www.Archive.org].*

*Primary Examiner* — William Allen
(74) *Attorney, Agent, or Firm* — Michael A. Kerr; Kerr IP Group, LLC

(57) ABSTRACT

A system and method for ordering a plurality of tablets is described. The system comprises a server accessible via a network by at least one client. An online application is hosted on the server and accessible by the client. The online application comprises a user interface configured to receive a first input associated with a first tablet. The first input comprises a first schedule for consumption of the first tablet. The user interface is also configured to receive a second input associated with a second tablet. The second input comprises a second schedule for consumption of the second tablet. The user interface is further configured to display an integrated schedule comprising the schedule for consumption of the first tablet and the schedule for consumption of the second tablet.

19 Claims, 24 Drawing Sheets

(56) References Cited

U.S. PATENT DOCUMENTS

| | | |
|---|---|---|
| 3,933,245 A | 1/1976 | Mullen |
| 4,039,080 A | 8/1977 | Cappuccilli |
| 4,062,445 A | 12/1977 | Moe |
| 4,318,477 A | 3/1982 | Kerpe |
| 4,416,375 A | 11/1983 | Braverman et al. |
| 4,512,476 A | 4/1985 | Herrington, Jr. |
| 4,535,890 A | 8/1985 | Artusi |
| 4,546,901 A | 10/1985 | Buttarazzi |
| 4,655,026 A | 4/1987 | Wigoda |
| 4,693,371 A | 9/1987 | Malpass |
| 4,749,085 A | 6/1988 | Denney |
| 4,799,590 A | 1/1989 | Furman |
| 4,805,800 A | 2/1989 | Nocek et al. |
| 4,811,764 A | 3/1989 | McLaughlin |
| 4,850,489 A | 7/1989 | Weithmann et al. |
| 4,860,899 A | 8/1989 | McKee |
| 4,867,315 A | 9/1989 | Baldwin |
| 4,872,559 A | 10/1989 | Schoon |
| 4,887,790 A | 12/1989 | Wilkinson et al. |
| 4,918,604 A | 4/1990 | Baum |
| 4,953,745 A | 9/1990 | Rowlett, Jr. |
| 4,972,657 A | 11/1990 | McKee |
| 5,014,851 A | 5/1991 | Wick |
| 5,085,510 A | 2/1992 | Mitchell |
| 5,186,345 A | 2/1993 | Ching An |
| 5,195,123 A | 3/1993 | Clement |
| 5,199,636 A | 4/1993 | Young |
| 5,310,057 A | 5/1994 | Caldwell et al. |
| 5,366,087 A | 11/1994 | Bane |
| 5,390,796 A | 2/1995 | Kerfoot, Jr. |
| 5,422,831 A | 6/1995 | Misra et al. |
| 5,457,895 A | 10/1995 | Thompson et al. |
| 5,505,371 A | 4/1996 | O'Neill |
| 5,522,512 A | 6/1996 | Archer et al. |
| 5,558,229 A | 9/1996 | Halbich |
| 5,577,612 A | 11/1996 | Chesson et al. |
| 5,597,995 A | 1/1997 | Williams et al. |
| 5,642,906 A | 7/1997 | Foote et al. |
| 5,671,592 A | 9/1997 | Yuyama et al. |
| 5,737,539 A | 4/1998 | Edelson et al. |
| 5,746,323 A | 5/1998 | Dragotta |
| 5,788,079 A | 8/1998 | Bouthiette |
| 5,788,974 A | 8/1998 | D'Amico et al. |
| D400,412 S | 11/1998 | Gold |
| 5,873,466 A | 2/1999 | Hulick |
| 5,878,887 A | 3/1999 | Parker et al. |
| 5,883,370 A | 3/1999 | Walker et al. |
| 5,899,333 A | 5/1999 | Williams et al. |
| 5,921,398 A | 7/1999 | Carroll |
| 5,963,453 A | 10/1999 | East |
| 5,995,938 A | 11/1999 | Whaley |
| 6,012,582 A | 1/2000 | Haygeman et al. |
| 6,021,392 A | 2/2000 | Lester et al. |
| 6,021,623 A | 2/2000 | Bouthiette |
| 6,023,916 A | 2/2000 | Bouthiette |
| 6,066,374 A | 5/2000 | Healy et al. |
| 6,068,156 A | 5/2000 | Liff et al. |
| 6,077,530 A | 6/2000 | Weinstein et al. |
| 6,115,996 A | 9/2000 | Yuyama et al. |
| 6,129,211 A | 10/2000 | Prakken et al. |
| 6,155,423 A | 12/2000 | Katzner et al. |
| 6,155,485 A | 12/2000 | Coughlin et al. |
| 6,170,230 B1 | 1/2001 | Chudy et al. |
| 6,202,923 B1 | 3/2001 | Boyer et al. |
| 6,227,371 B1 | 5/2001 | Song |
| 6,273,260 B1 | 8/2001 | ColDepietro et al. |
| 6,293,403 B1 | 9/2001 | Holmberg |
| 6,308,494 B1 | 10/2001 | Yuyama et al. |
| 6,317,648 B1 | 11/2001 | Sleep et al. |
| 6,318,630 B1 | 11/2001 | Coughlin et al. |
| 6,324,253 B1 | 11/2001 | Yuyama et al. |
| 6,330,351 B1 | 12/2001 | Yasunaga |
| 6,343,695 B1 | 2/2002 | Petrick et al. |
| D455,057 S | 4/2002 | Medhurst |
| 6,371,297 B1 | 4/2002 | Cha |
| 6,378,572 B1 | 4/2002 | Neubauer et al. |
| 6,401,919 B1 | 6/2002 | Griffis et al. |
| 6,449,921 B1 | 9/2002 | Kim |
| 6,449,927 B2 | 9/2002 | Hebron et al. |
| 6,460,693 B1 | 10/2002 | Harrold |
| 6,505,461 B1 | 1/2003 | Yasunaga |
| 6,523,694 B2 | 2/2003 | Lux, Jr. et al. |
| 6,527,138 B2 | 3/2003 | Pawlo et al. |
| 6,535,637 B1 | 3/2003 | Wootton et al. |
| 6,564,945 B1 | 5/2003 | Weinstein et al. |
| 6,581,798 B2 | 6/2003 | Liff et al. |
| 6,594,928 B1 | 7/2003 | Clawson et al. |
| 6,611,733 B1 | 8/2003 | De La Huerga |
| 6,662,081 B1 | 12/2003 | Jacober et al. |
| 6,681,935 B1 | 1/2004 | Lewis |
| 6,690,998 B1 | 2/2004 | Yuyama |
| 6,711,460 B1 | 3/2004 | Reese |
| 6,735,497 B2 | 5/2004 | Wallace et al. |
| 6,738,723 B2 | 5/2004 | Hamilton |
| 6,757,898 B1 | 6/2004 | Ilsen et al. |
| 6,771,369 B2 | 8/2004 | Rzasa |
| 6,839,403 B1 | 1/2005 | Kotowski et al. |
| 6,892,512 B2 | 5/2005 | Rice et al. |
| 6,925,774 B2 | 8/2005 | Peterson |
| 6,981,592 B2 | 1/2006 | Siegel |
| 7,006,893 B2 | 2/2006 | Hart et al. |
| 7,010,899 B2 | 3/2006 | McErlean et al. |
| 7,017,748 B2 | 3/2006 | Weinstein |
| 7,028,723 B1 | 4/2006 | Alouani et al. |
| 7,055,294 B1 | 6/2006 | Lewis |
| 7,111,780 B2 | 9/2006 | Broussard et al. |
| 7,185,476 B1 | 3/2007 | Siegel et al. |
| 7,225,597 B1 | 6/2007 | Knoth |
| 7,398,279 B2 | 7/2008 | Muno et al. |
| 7,426,814 B2 | 9/2008 | Knoth |
| 7,509,787 B2 | 3/2009 | Ballestrazzi et al. |
| 7,668,730 B2 | 2/2010 | Reardan et al. |
| 7,828,148 B2 | 11/2010 | Gibson |
| 8,055,512 B1 | 11/2011 | Pankow et al. |
| 8,122,849 B2 | 2/2012 | Clarke et al. |
| 8,146,747 B2 | 4/2012 | Luciano et al. |
| 8,196,774 B1 | 6/2012 | Clarke et al. |
| 8,266,878 B2 | 9/2012 | Luciano et al. |
| 8,712,582 B1 | 4/2014 | Luciano et al. |
| 8,713,897 B2 | 5/2014 | Luciano et al. |
| 8,777,012 B2 | 7/2014 | Luciano et al. |
| 8,789,700 B2 | 7/2014 | Luciano et al. |
| 8,914,298 B1 | 12/2014 | Luciano |
| 8,931,241 B2 | 1/2015 | Luciano et al. |
| 8,972,288 B2 | 3/2015 | Luciano, Jr. |
| 2001/0041968 A1 | 11/2001 | Hamilton |
| 2002/0029223 A1 | 3/2002 | Rice et al. |
| 2002/0042725 A1 | 4/2002 | Mayaud |
| 2002/0047019 A1 | 4/2002 | Devers |
| 2002/0066691 A1 | 6/2002 | Varon |
| 2002/0104778 A1 | 8/2002 | Lux et al. |
| 2002/0117405 A1 | 8/2002 | Wang et al. |
| 2003/0012701 A1 | 1/2003 | Sangha et al. |
| 2003/0018495 A1 | 1/2003 | Sussman |
| 2003/0136698 A1 | 7/2003 | Klatt |
| 2003/0142784 A1 | 7/2003 | Suzuki et al. |
| 2003/0174326 A1 | 9/2003 | Rzasa et al. |
| 2003/0193185 A1 | 10/2003 | Valley et al. |
| 2003/0200726 A1 | 10/2003 | Rast |
| 2003/0209461 A1 | 11/2003 | French et al. |
| 2004/0011806 A1 | 1/2004 | Luciano et al. |
| 2004/0011961 A1 | 1/2004 | Platt et al. |
| 2004/0045863 A1 | 3/2004 | Rhoades |
| 2004/0069674 A1 | 4/2004 | Siegel |
| 2004/0069675 A1 | 4/2004 | Stevens |
| 2004/0088187 A1 | 5/2004 | Chudy et al. |
| 2004/0094050 A1 | 5/2004 | Ackley, Jr. et al. |
| 2004/0122713 A1 | 6/2004 | Hill, Sr. et al. |
| 2004/0123564 A1 | 7/2004 | McErlean et al. |
| 2004/0140241 A1 | 7/2004 | Weinstein |
| 2004/0158507 A1 | 8/2004 | Meek et al. |
| 2004/0162634 A1 | 8/2004 | Rice et al. |
| 2004/0172295 A1 | 9/2004 | Dahlin et al. |
| 2004/0188998 A1 | 9/2004 | Henthorn |

(56) References Cited

U.S. PATENT DOCUMENTS

| | | |
|---|---|---|
| 2004/0217038 A1 | 11/2004 | Gibson |
| 2004/0225528 A1 | 11/2004 | Brock |
| 2004/0243445 A1 | 12/2004 | Keene |
| 2004/0249591 A1 | 12/2004 | Trebbi |
| 2004/0256277 A1 | 12/2004 | Gedanke |
| 2004/0260424 A1 | 12/2004 | Mahar |
| 2004/0268413 A1 | 12/2004 | Reid et al. |
| 2005/0021367 A1 | 1/2005 | Saeger et al. |
| 2005/0044762 A1 | 3/2005 | Alturi |
| 2005/0049746 A1 | 3/2005 | Rosenblum |
| 2005/0049747 A1 | 3/2005 | Willoughby et al. |
| 2005/0060197 A1 | 3/2005 | Mayaud |
| 2005/0061825 A1 | 3/2005 | Willoughby et al. |
| 2005/0144038 A1 | 6/2005 | Tamblyn et al. |
| 2005/0171813 A1 | 8/2005 | Jordan |
| 2005/0209879 A1 | 9/2005 | Chalmers |
| 2005/0218152 A1 | 10/2005 | Simon |
| 2005/0269817 A1 | 12/2005 | Alasia et al. |
| 2006/0045323 A1 | 3/2006 | Ateya |
| 2006/0065670 A1 | 3/2006 | Doublet et al. |
| 2006/0076262 A1 | 4/2006 | Bassett |
| 2006/0122729 A1 | 6/2006 | Murphy et al. |
| 2006/0124502 A1 | 6/2006 | Lee |
| 2006/0163869 A1 | 7/2006 | Adler et al. |
| 2006/0213816 A1 | 9/2006 | Jorritsma |
| 2006/0219595 A1 | 10/2006 | Peters |
| 2007/0000805 A1 | 1/2007 | Van Den Brink |
| 2007/0168228 A1 | 7/2007 | Lawless |
| 2007/0173971 A1 | 7/2007 | Richardson et al. |
| 2007/0210164 A1 | 9/2007 | Conlon et al. |
| 2008/0059228 A1 | 3/2008 | Bossi et al. |
| 2008/0142400 A1 | 6/2008 | Arnold |
| 2008/0190076 A1 | 8/2008 | Klingel et al. |
| 2008/0228160 A1 | 9/2008 | Harrison |
| 2009/0119129 A1* | 5/2009 | Nadas et al. ................. 705/3 |
| 2009/0230013 A1 | 9/2009 | Born et al. |
| 2010/0069213 A1 | 3/2010 | Luciano et al. |
| 2010/0100391 A1* | 4/2010 | Daya et al. ................... 705/2 |
| 2010/0147734 A1 | 6/2010 | Luciano, Jr. et al. |
| 2010/0153129 A1 | 6/2010 | Luciano et al. |
| 2010/0265072 A1 | 10/2010 | Goetz et al. |
| 2010/0324728 A1* | 12/2010 | Rosenblum ................. 700/242 |
| 2011/0036856 A1* | 2/2011 | van Ooyen et al. ......... 221/123 |
| 2011/0040572 A1 | 2/2011 | Chmiel et al. |
| 2011/0100863 A1 | 5/2011 | Luciano |
| 2011/0101016 A1 | 5/2011 | Luciano, Jr. |
| 2011/0161097 A1 | 6/2011 | Fox et al. |
| 2011/0251850 A1* | 10/2011 | Stephens ........................ 705/2 |
| 2012/0022893 A1 | 1/2012 | Findlay et al. |
| 2012/0089416 A1 | 4/2012 | Luciano, Jr. |
| 2012/0116579 A1 | 5/2012 | Shows et al. |
| 2012/0123907 A1 | 5/2012 | Luciano |
| 2012/0186693 A1 | 7/2012 | Luciano et al. |
| 2012/0290129 A1 | 11/2012 | Luciano et al. |
| 2012/0296592 A1 | 11/2012 | Luciano et al. |
| 2012/0312714 A1 | 12/2012 | Luciano et al. |
| 2013/0161207 A1 | 6/2013 | Luciano et al. |

FOREIGN PATENT DOCUMENTS

| | | |
|---|---|---|
| WO | WO 2004/082561 A1 | 9/2004 |
| WO | WO 2005/102841 | 11/2005 |

* cited by examiner

SYSTEM AND METHOD FOR ONLINE INTEGRATED MULTIPLE TABLET ORDERING

FIELD

This description relates to a system and method for receiving a multiple tablet order with an online application. More particularly, the description relates to a associating dosing schedules with multiple tablet orders and displaying an integrated schedule to a user with an online application.

BACKGROUND

One of the major problems in taking prescribed daily medications emanates from patients having to take multiple doses of medications, vitamins, supplements, etc. at various dosing periods during the day. A principal concern is determining whether all medications have been taken in compliance with the daily regimen.

The fear of taking improper dosages can be particularly acute in the elderly, many of whom have some degree of mental dementia and can easily be confused as to whether they have taken all of their medications at the correct time. Some patients have difficulty sorting out the medications prior to taking them and taking the medication in a timely manner. Providing medications to elderly, disabled or incapacitated individuals can also be complicated because one caregiver may oversee the medication of many patients.

One solution to the problem of taking multiple medications is to pre-package the multiple medications so that users can take the pre-packaged medications at a predetermined time. Generally, these methods of pre-packaging medications are targeted to patients that may lack maturity or mental capacity to take the correct medications at the correct time. For example, young children in a school or campground, and elderly individuals in elder care centers, or nursing homes are target groups for the pre-packaging of medications. Some of the pre-packaged medications are placed in a small plastic bag, which may be easily misplaced. Other pre-packaged medications are placed in sealed cups that are difficult to open.

Furthermore, pre-packaged multiple medications are difficult to order because the pre-packaging of multiple medications is a specialty service that has not been automated. The manual ordering systems are expensive to administer because they lack automation. Therefore, there is a need for a highly automated ordering system and process that is simple and cost effective for a patient or a pharmacist to use. An automated system and method for receiving orders would make it substantially easier to process a multiple prescription order, which would in turn make the process much more cost effective.

Although multiple prescription filling systems are available, e.g. the McKesson PACMED system, these systems have limited labeling capabilities. Additionally, these filling systems do not have procedures to verify the multiple prescription order before filling a pouch or cup. Furthermore, these filling systems fail to provide a method for assembling a multiple prescription order that can be easily transported and administered, so that the multiple medications can be taken at the appropriate time. Further still, these filling systems fail to verify that each pouch in a filled prescription order has the appropriate medication.

SUMMARY

A system for online ordering of a plurality of tablets is described. The system comprises a server accessible via a network by at least one client. An online application is hosted on the server and accessible by the client. The online application comprises a user interface configured to receive a first input associated with a first tablet. The first input comprises a first schedule for consumption of the first tablet. The user interface is also configured to receive a second input associated with a second tablet. The second input comprises a second schedule for consumption of the second tablet. The user interface is further configured to display an integrated schedule comprising the schedule for consumption of the first tablet and the schedule for consumption of the second tablet.

A system for online ordering of a plurality of tablets according to another embodiment comprises a database hosted on the server. The database comprises information associated with a plurality of tablet types. An online application hosted on the server comprises a user interface configured to receive a search parameter and display a subset of data from the database corresponding to the search parameter. The user interface receives a first input associated with a first tablet. The first input comprises a first schedule for consumption of the first tablet. The user interface is also configured to receive a second input associated with a second tablet. The second input comprises a second schedule for consumption of the second tablet. The user interface is further configured to display an integrated schedule comprising the schedule for consumption of the first tablet and the schedule for consumption of the second tablet.

A method for online ordering of a plurality of tablets is also described. The method comprises receiving a first input with an online application, the first input comprising a first schedule for consumption of the first tablet. The method further comprises receiving a second input with the online application, the second input comprising a second schedule for consumption of the second tablet. The method also comprises displaying an integrated schedule with the online application, the integrated schedule comprising the schedule for consumption of the first tablet and the schedule for consumption of the second tablet.

DRAWINGS

The present invention will be more fully understood by reference to the following drawings which are for illustrative, not limiting, purposes.

DESCRIPTION

Figure 1:
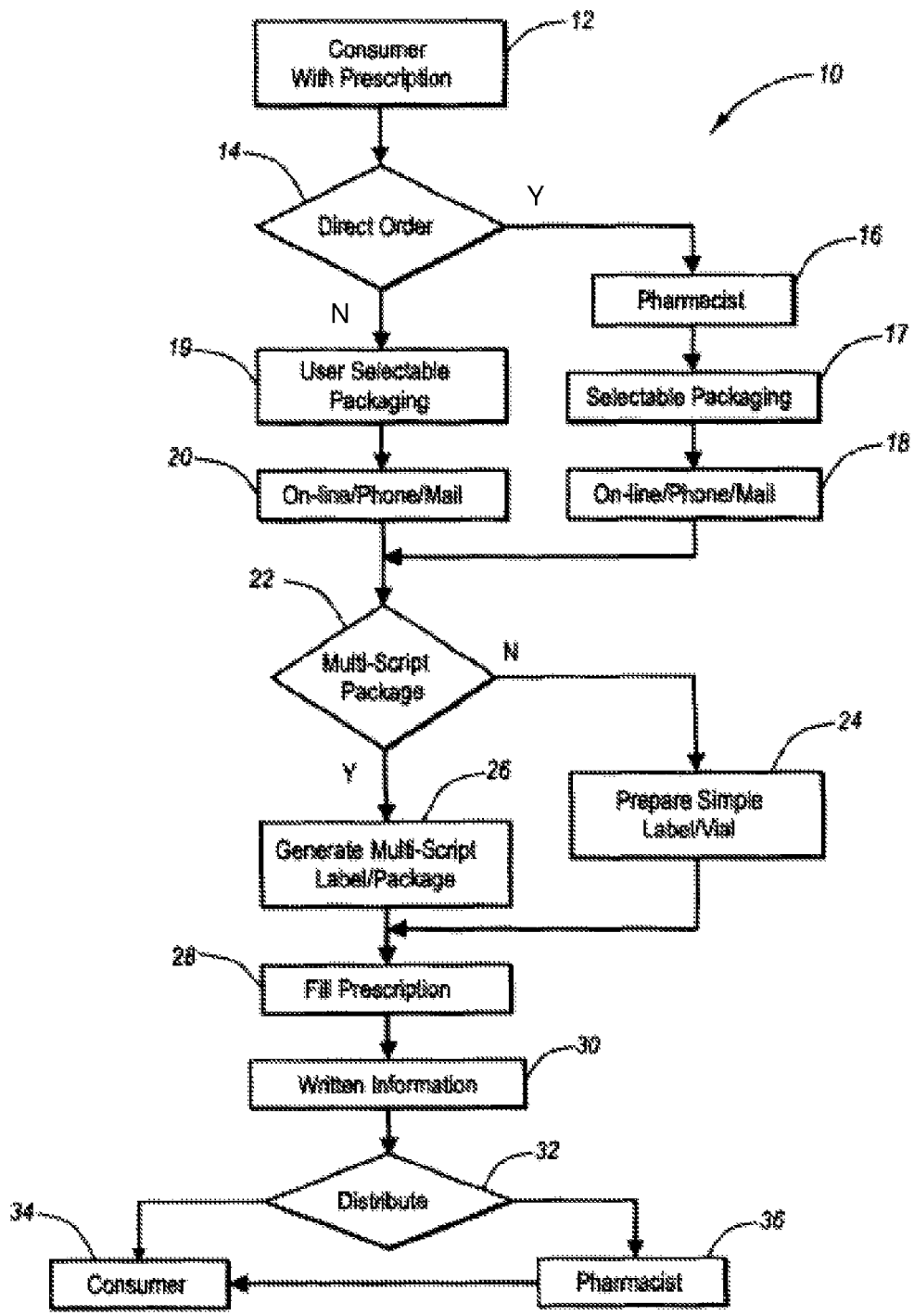
FIG. 1 is an illustrative flowchart showing a method for receiving and processing at least one prescription.

Persons of ordinary skill in the art will realize that the following description is illustrative and not in any way limiting. Other embodiments of the claimed subject matter will readily suggest themselves to such skilled persons having the benefit of this disclosure. It shall be appreciated by those of ordinary skill in the art that the systems and apparatus described hereinafter may vary as to configuration and as to details. Additionally, the methods may vary as to details, order of the actions, or other variations without departing from the illustrative methods disclosed herein.

An online application that allows a user to order tablets and indicate dosage scheduling for the tablets is described. The online application is hosted on a server that is communicably coupled to the network. The online application may be accessed by a user through a client such as a personal computer that is communicably coupled to the network. The online application presents a user interface that allows the user to search among the tablets available through the application. For example, the online application may be configured to access a database that stores information about tablet types accessible through the application. The database may be hosted on the same server as the server that hosts the online application, or may be hosted on another server communicably coupled to the network.

The "online application" may also be referred to as an "ordering application" or an "online ordering application." The terms are used interchangeably to refer to an online application enabling ordering of tablets.

Once the user has located a desired tablet, the user may place an order for the tablet. The user interface allows the user to indicate a schedule of consumption for the tablet. For example, the user may indicate a number of tablets to be consumed during AM, afternoon, and PM dosing periods. The user may be able to indicate days of the week on which the tablet is to be consumed, to indicate that the tablet is to be consumed every day, every other day, or to indicate an every other day schedule for a first tablet that is offset from an every other day schedule for a second tablet. The user may also be able to indicate that consumption of the tablet is to increase or decrease over time.

The user may then locate a next desired tablet, place an order for the next desired tablet, and indicate a schedule of consumption for the next desired tablet. The user may continue to order additional tablets until the user has ordered all desired tablets. When the user is ready to place the complete order, the user is presented with a display of all ordered tablets indicating the schedule for each tablet. In this manner, the user can verify that the schedule of consumption for each tablet is correct.

When the user has confirmed the complete order, the online application may generate an integrated order for dispensing. The integrated order may be received by a filling machine, which may then assemble the ordered tablets into pouches. The ordered tablets may be packaged such that one pouch contains all tablets to be consumed during a particular dosing period. For example, a pouch may contain all tablets to be consumed during the AM dosing period on a Monday. The pouches may be combined into a secondary package, for example, a package containing all the pouches for consumption during a particular week or month.

The ordering system described herein may operate with any front-end pharmacy solution and any back-end automated filling robot. The goal is to integrate prescription or other tablet orders by combining the orders and generating an output.

In some embodiments, a database stores tablet information such as identifying information, an image of the tablet, side effects, manufacturer, generic/brand name status, and whether a prescription is required for dispensing the tablet. The integrated order information with some or all of its associated information may be collated into a booklet that is referred to as a patient information booklet that may additionally include information about the patient. A label containing information about the tablets contained in a particular pouch may be affixed to the pouch. The label may additionally include information about the patient. A secondary label indicating information about the tablets contained in the pouches contained in a secondary container may be affixed to the secondary container. The secondary label may additionally include information about the patient.

Tablets as used herein may refer to any form of prescription or non-prescription medication in the form of caplets, pills, capsules, powders, liquids, gels, or suppositories, including vitamins, supplements, herbal formulations, or combinations thereof, intended to be ingested by or administered to a patient to improve the patient's health or well being. In this patent, the term "tablets" is used interchangeably with medications, pharmaceuticals and nutraceuticals.

FIGS. 1-17 below indicate generally systems and methods for receiving, processing and filling tablet orders. FIGS. 18-22 present illustrative embodiments of a system and method for allowing a user to order tablets and indicate dosage scheduling for the tablets using an online application.

Referring to FIG. 1 there is shown a flowchart 10 illustrating a general method for receiving and processing at least one order. The illustrative order is a prescription order. Additionally, the illustrative order may include other tablets as described herein. A prescription generally comprises at least one medication that is dispensed as a tablet. The method may be initiated with a user having a doctor's prescription at block 12. By way of example and not of limitation, a user may be a patient or caregiver. A user may also be a person or entity authorized to conduct a transaction for at least one product that includes prescription medication, over-the-counter medication, vitamins, supplements, herbs, oils, or any such substances. A prescription may not be required for processing a prescription order. For example, a prescription may not required for dispensing certain tablets such as vitamins, herbs, oils, over-the-counter medications, supplements, and other such products. Additionally, in some jurisdictions a prescription for dispensing medications may not be required.

A direct order may then be placed at decision diamond 14. For the illustrative prescription order, a "direct order" is an order that must be placed by a pharmacist. An order is placed using a graphical user interface (GUI) resident on a browser running on a computer that is in communication with the Internet by a pharmacist, patient, customer, or caregiver. If the order requires a pharmacist (i.e., if it is a direct order), the method proceeds to block 16 where a pharmacist places the order for the appropriate medications. After block 16, the method proceeds to block 17 in which the pharmacist may be prompted for at least one packaging option. A variety of different packaging options may be provided to the pharmacist. The packaging options may comprise at least one multiple prescription container as described in further detail below. Alternatively, as described by block 18, the order may also be placed by telephone, fax, mail, scanned order, or any other such means for placing an order that does not employ a graphical user interface.

If the order can be placed without the need for a pharmacist, the method proceeds to block 19 where the user is prompted to select at least one packaging option. Generally, the user is either a patient, a customer ("users" together), or a caregiver. A variety of packaging options may be provided to the caregiver or user. As described above, the order may also be placed on-line, by telephone, fax, mail, or other such means for communicating the order.

After receiving an order, the method proceeds to decision diamond 22 where a decision about how to process a multiple prescription order is made. As used herein, a multiple prescription order is also referred to as a "Multi Script" order as well as a multiple tablet order. Broadly, a multiple prescription order is an order that comprises two or more tablets. A first tablet may be different from or the same as a second tablet.

A multiple prescription order comprises more than one type of tablet to be taken at approximately the same time on the same date. If the order is not a multiple prescription order, the method proceeds to block 24, in which a single vial is prepared with a simple label. However, if the order is a multiple prescription order, the method proceeds to block 26 where a multiple prescription container is selected and the appropriate label is generated. At block 28, either the simple vial or the multiple prescription container is filled.

At block 30, a plurality of written information may also be generated. This plurality of information may include information related to each medication, summary information about each medication, appropriate labeling, some summary information about the patient, a drug interaction report, or any such combination thereof. The drug interaction report may provide information to help individuals properly take the prescribed medication. The drug interaction report includes information about the various drug interactions that may be associated with each prescription. For example, certain foods may interact with a particular prescription. Additionally, there may be a group of particular drugs that may interact with the prescription, and this information may not be readily available to the patient or the patient's caregiver. The drug interaction report may be used to help identify foods, medications, vitamins, supplements, or any combination thereof that may interact with the patient's filled prescription. The written information may also include a summary of the medications being taken as described in further detail below.

The method then proceeds to decision diamond 32 where a decision is made about how to distribute the filled order. If the filled order must be distributed to a pharmacist 36, the pharmacist 36 provides the prescription to the user 34 that may be a patient, caregiver, or customer. Alternatively, the filled prescription may be distributed directly to the particular user 34.

Figure 2:
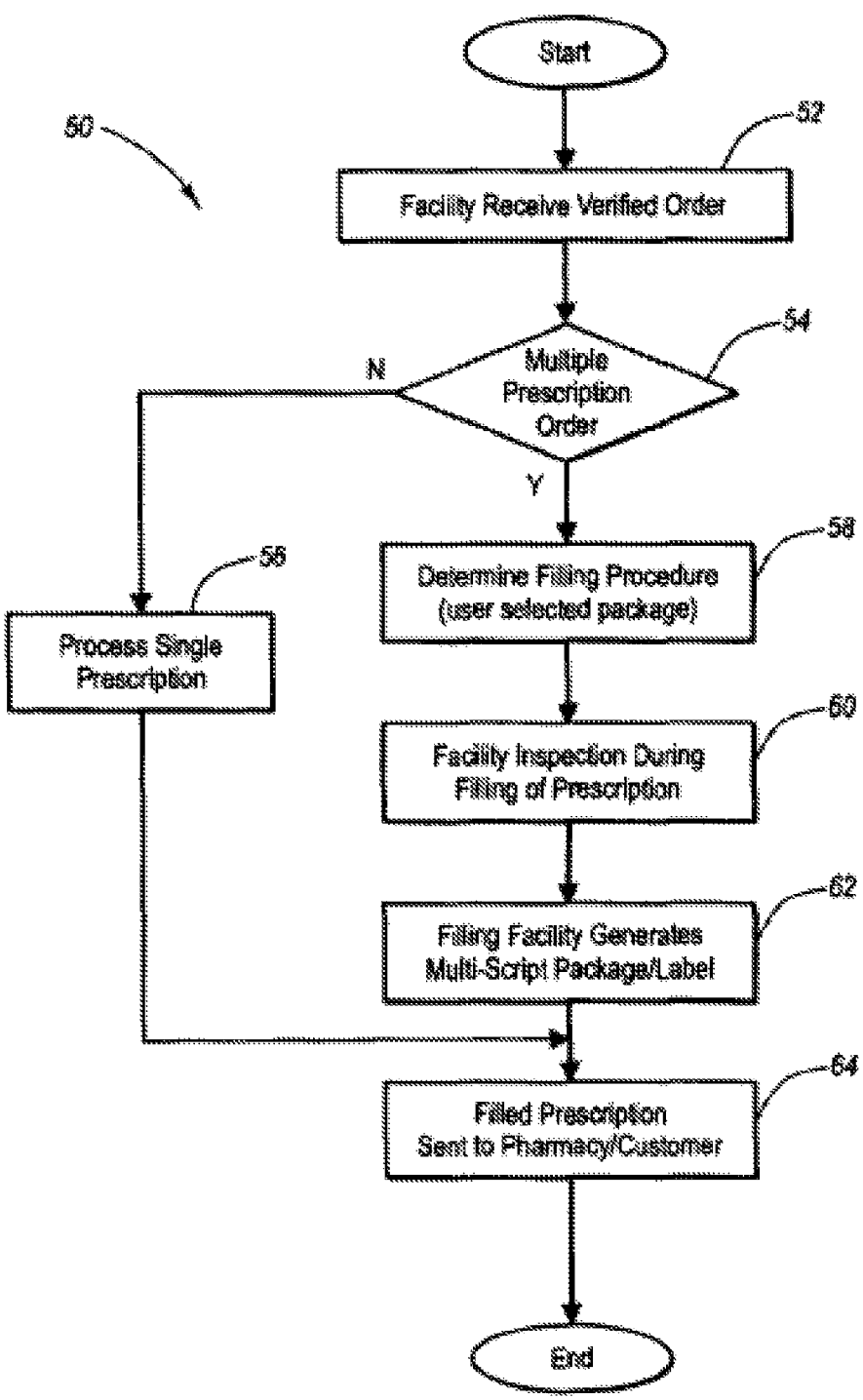
FIG. 2 is an illustrative high-level flowchart of a production facility processing a prescription order.

Referring to FIG. 2, there is shown an illustrative high-level flowchart 50 of a production facility processing a prescription order. Recall, FIG. 1 describes a general method for receiving and processing a prescription order. FIG. 2 provides an illustrative flowchart from the perspective of a production facility processing an illustrative verified prescription order. The method is initiated at block 52 where the production facility receives the illustrative verified prescription order. The verified prescription order is an order that has been "verified" according to local jurisdictional requirements, insurance requirements, co-pay requirements, transactional requirements, or a combination thereof. For example, in certain jurisdictions the verified prescription order may require a medical doctor's signature, and may have to be processed by a pharmacist. Additionally, the verified order may require approval from an insurance company, Medicare or any such entity. In other jurisdictions, the only form of verification may include confirming that funds are available from the particular individual or organization charged, which satisfies transactional requirements. By way of example and not of limitation, verification of the availability of funds may include simply receiving authorization to charge a credit card and confirming that the credit card is a valid card.

The method then proceeds to decision diamond 54 where a determination is made whether the verified order was a multiple prescription order. If the order is not a multiple prescription order, the method proceeds to block 56 where a single prescription order is processed, and then subsequently the filled prescription is sent to a pharmacy or customer as shown in block 64.

If the verified prescription order is a multiple prescription order, the method proceeds to block 58 where the facility determines the filling procedure to use. The filling procedure will depend on a host of variables such as the type of user selectable packaging. The method then proceeds to block 60 where the production facility inspects the tablets that have been placed in the multiple prescription containers. The type of inspection depends on the particular design of the production facility. For example the inspection may be conducted by tablet counters, RFID counters, by using X-ray or near IR technology, or other such technology capable of inspecting the multiple prescription containers. Alternative methods of inspecting the filled multiple prescription will readily suggest themselves to those of ordinary skill in the art.

After completing the inspection, the production facility generates the plurality of written information shown in block 62. The written information may also be referred to as packaging information. The written information may comprise information about each substance, appropriate labeling, summary information as described below, a drug interaction report as described in this specification, or a combination thereof. At block 64, the filled prescription order is then sent to a designated entity or individual including, but not limited to, the patient, the caregiver, the pharmacist, the user, or the user.

Figure 3:
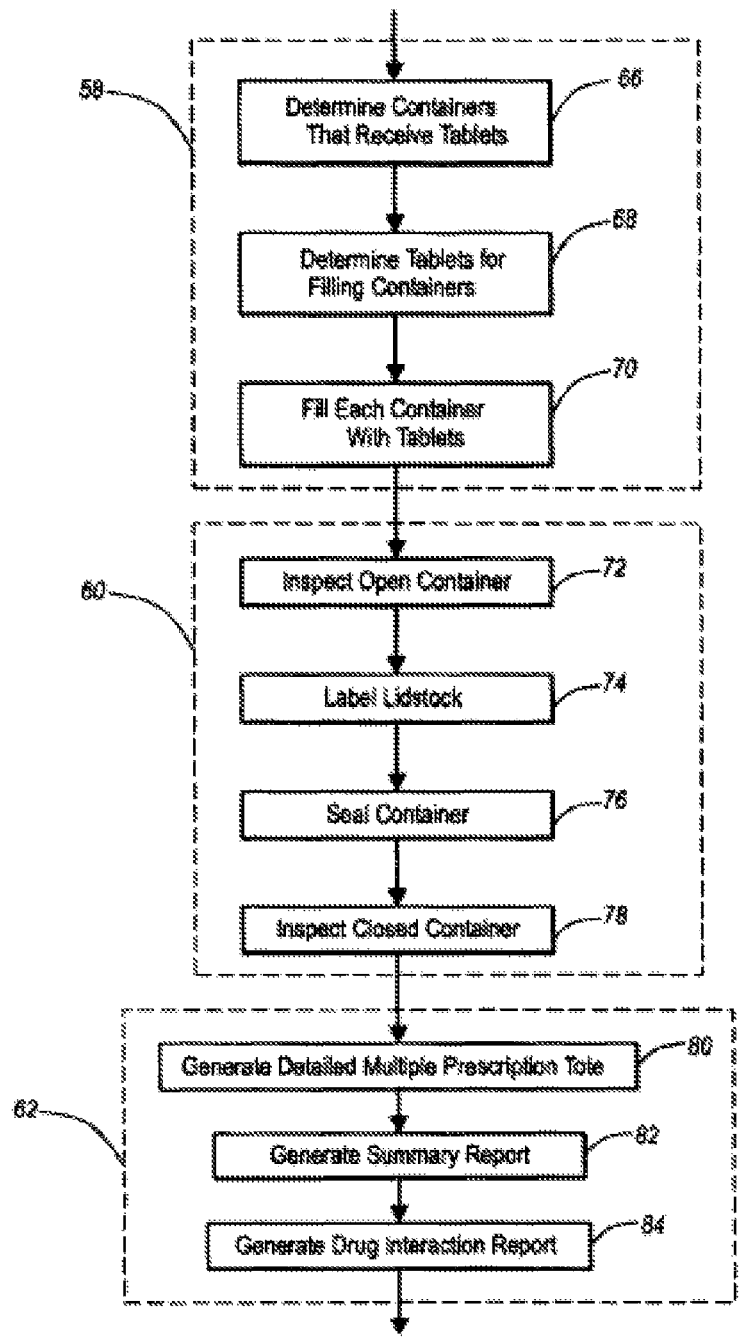
FIG. 3 is a more detailed flowchart showing how a multiple prescription order is processed within the production facility.

Referring to FIG. 3, there is shown a more detailed flowchart of a multiple prescription order being processed within the production facility. A more detailed view of block 58 is shown in FIG. 3, which includes a description of the user selectable packaging that may be determined by the user, user, patient, caregiver, or pharmacist. In the illustrative embodiment, a variety of different packaging options are presented. By way of example and not of limitation, the verified prescription order may include 10 tablets taken three times per day, which requires mid-size multiple prescription containers. In another example, the patient and/or user may desire a package design that may be easily used by a caregiver. In yet another illustrative example, the patient may want a package design that is small and portable. Based on the user's needs, the appropriate user selectable options may be provided. Thus, an individual requesting the filling of a multiple prescription order will provide sufficient information so that appropriately sized containers are identified as represented by block 66. The containers may be stacked. In certain embodiments, the containers may be placed on a conveyer belt system which allows the containers to travel along the conveyor system to the designated filler module containing the correct medications. The containers may also be placed on trays configured to hold a plurality of containers and situated on a conveyor system which allows the filling facility to track the position of each container within the filling facility.

Additionally, sufficient information is provided so that the appropriate tablets can be associated with the appropriate multiple prescription containers at the appropriate dosing times as represented by block 68. A multiple prescription container holds a multiple prescription order. The method then proceeds to block 70 where each of the multiple prescription containers or pouches is filled with the appropriate tablets. A more detailed explanation of the method for filling each of the multiple prescription containers is described in further detail below.

A more detailed view of block 60 where the production facility inspects the containers is also described. The inspection may be conducted either before or after the multiple prescription containers are sealed as represented by block 72. A label may then be printed on lidstock 74 and the multiple prescription container may then be sealed 76. Additionally, the medications within the multiple prescription container may be inspected after the multiple prescription containers are sealed as represented by block 78. Thus, the filled multiple prescription container may be inspected either before the multiple prescription containers is sealed, after the multiple prescription container is sealed, or both.

A more detailed view of block 62 is also presented in FIG. 3 where after the inspection 60, the production facility generates the plurality of written information. The written information may also be referred to as packaging information. The written information may comprise information about each substance which is described in the multiple prescription tote 80. The written information may also include summary information about the various medications and is represented by block 82. A drug interaction report may also be generated at block 84.

Figure 4:
FIG. 4 shows an illustrative label that is generated by the production facility.

Referring to FIG. 4 there is shown an illustrative label that is generated by the production facility. By way of example and not of limitation, the illustrative label 160 may contain written information that is related to each medication such as summary information about each medication, summary information about the patient, the name of the patient, an image of the patient, images of the first tablet and the second tablet that may be to scale, a drug interaction description, or any combination thereof. The illustrative label may be folded and conveniently coupled to a multiple prescription container. For example, the illustrative label 160 can be coupled to a dispensing sleeve, which is described in further detail below.

The illustrative label 160 may include an image 162 of the particular patient, and the name and address 164 of the patient. Furthermore, there may be additional unique information about the patient printed on the label, such as the doctor's name 166 and telephone number, and health insurance information. The label 160 also includes images 168 of the pills that have been prescribed. Additionally, there may be a particular description 170 about each pill on the folded label that may include manufacturer's latest labeling information, a summary of expected side effects 172, and a short description of possible drug interactions 174. This information may be presented in a manner similar to the Physician's Desk Reference, which includes a color picture of each pill with summary information about the pill. Additionally, information about how to administer products 176 may be provided. This information may be used by a caregiver to help in dispensing the appropriate medications.

Figure 5:
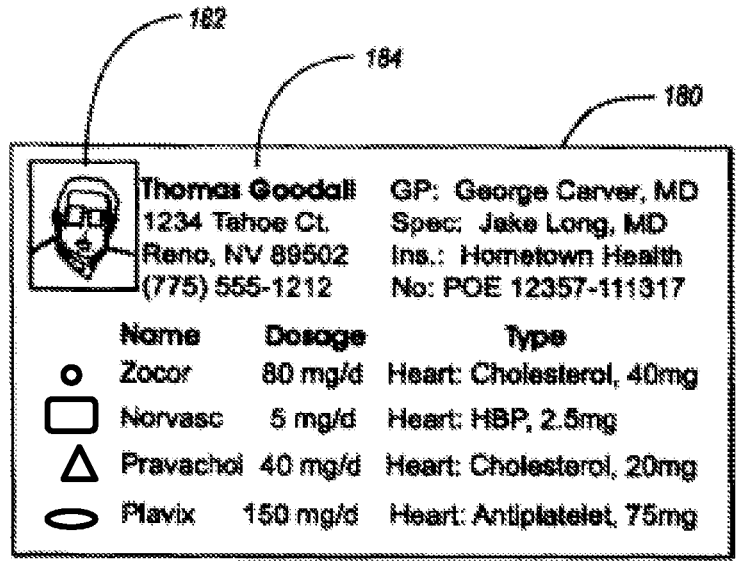
FIG. 5 is an illustrative summary label that may be generated by the production facility.
Figure 6:
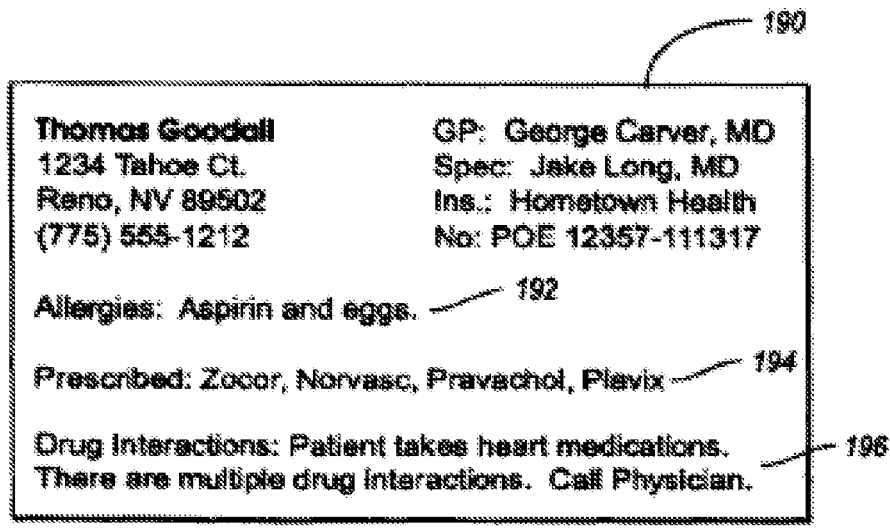
FIG. 6 is an alternative summary label that may be generated by the production facility.

Referring to FIG. 5 and FIG. 6 there are shown two different summary labels that may be generated by the production facility. In FIG. 5, the summary label 180 may be conveniently configured to fit into a wallet, or may be configured to be attached to the back of an insurance card or driver's license. The illustrative label 180 comprises an image 182 of the patient, images of the first tablet and the second tablet that are to scale, the patient name and address 184, and other such information. Information about the prescriptions and dosages may be provided with information about the patient's doctors and other health information. In FIG. 6, an alternative summary label 190 is shown that includes the patient's name, name of the patient's doctors, insurance, and insurance number. Additionally, summary label 190 includes information about the patient's allergies 192, the patient's prescriptions 194, and a warning about possible drug interactions 196. The particular summary label may be dependent on the patient's condition, the patient's caregiver, a physician's recommendation, statutory requirements, or any other such entity charged with assisting the patient.

Figure 7:
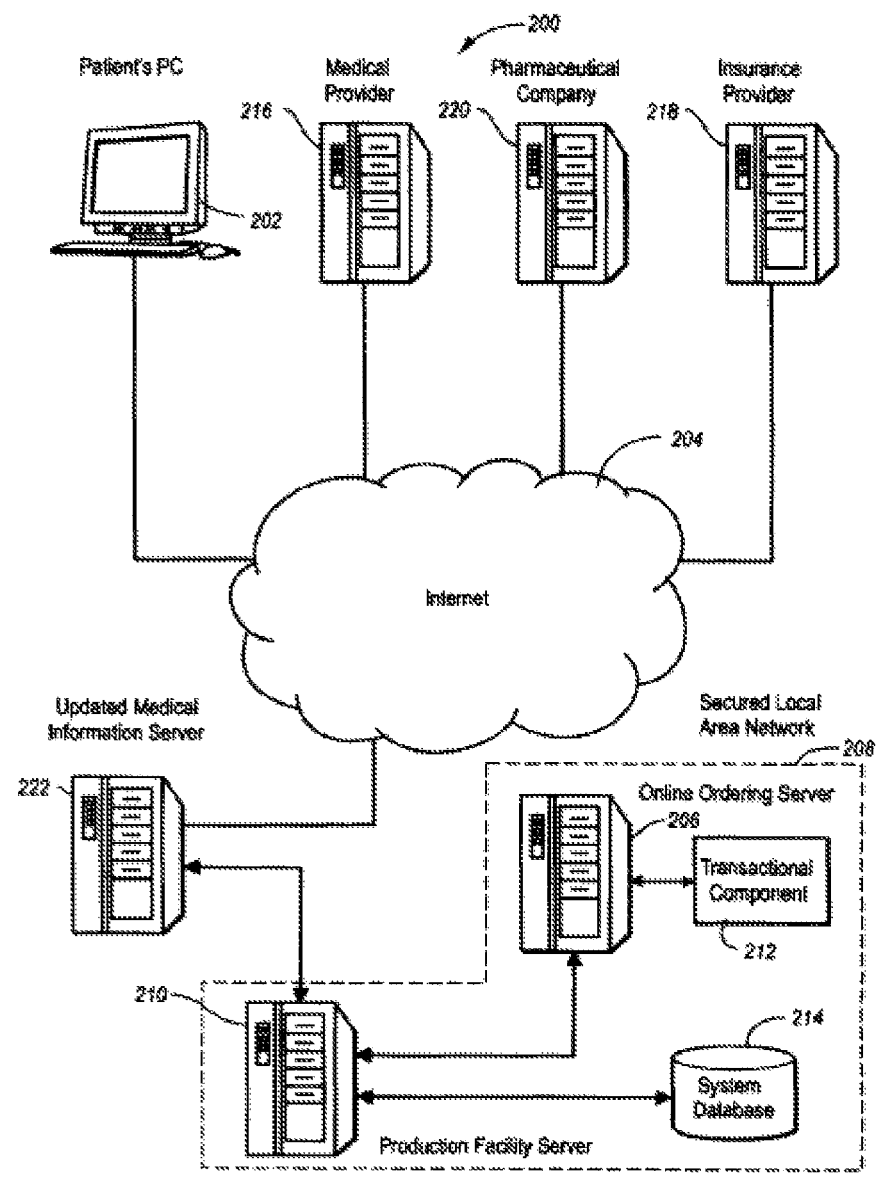
FIG. 7 is a block diagram of an illustrative system that receives a pill order via the Internet.

Referring to FIG. 7 there is shown a block diagram of an illustrative system 200 configured to receive an order for one or more tablets via a network. The illustrative client 202 displays the user interface of an online ordering application. The client may be any device capable of communication with a network, for example, a personal computer, laptop, or wireless device having a connection to the Internet. The illustrative client 202 is communicatively coupled to a wide area network such as the Internet 204.

The client 202 is configured to communicate with server 206. In some embodiments, the online server 206 is part of a secure local area network (LAN) 208 located at a production facility. Generally, the production facility is configured to generate a filled multiple prescription order as described throughout this specification. The production facility system may also comprise a production server 210, which may also be part of the secure LAN.

The online ordering server 206 is communicatively coupled to the production server 210. The online ordering server 206 is configured to host the ordering application.

The production server 210 controls the processing of the multiple prescription orders at the production facility that generates containers having a plurality of different tablets in each container. The illustrative production server 210 comprises a system database 214 that stores information about the products available at the production facility such as prescription medication, over-the-counter medication, vitamins, supplements, herbs, oils, or other such substances. Additionally, the system database 214 may include historical order information that is associated with the user. The database may further include information for each tablet type including identifying information, recommended usage, side effects and drug interactions, and other such information that would help the patient properly consume the products ordered by the patient. In one illustrative example, the production server contains and maintains information pertinent to the operation of the production facility. The production server 210 may be configured with management software that manages all the filling, inspection, printing, sealing, order tracking, and tablet assembly traffic control functions.

When an order is placed, the online application may request information from a medical provider server 216 or provide information to the medical provider server. For example, a medical provider such as a medical doctor or nurse can confirm that a specific medication has been ordered and will be administered in a particular manner. Additionally, the medical provider may also include notes for the patient on how the medicine should be taken, and this information may be printed by the production facility and associated with the patient's on-line order. Additionally, historical prescription order information may also be stored on the medical provider server 216.

The online application may also request information on the accuracy or changes in the end user's medical insurance from the insurance provider server 218. The online application may also request information from the pharmaceutical company server 220 about certain prescribed medications. These queries to the pharmaceutical company server 220 may occur during the online ordering process initiated by the end user or at various times when updating the system database. Additional queries may be made to government agencies, private medical facilities, on-line search engines, websites, databases, or any combination thereof.

The online ordering server 206 and/or the production facility server 210 may also be communicatively connected to an updated medical information server 222 via a network such as the Internet or a secure wide area network connection. The updated medical information server 222 may be a private or government maintained server with compiled updated information on the various drugs stored in the production facility. The updated information may comprise new warnings on drug interactions, updated expiration dates, toxicity information and the like. The updated information is communicated to the second labeling component. This information is valuable in assuring the multi-drug prescriptions are effective and safe.

Additionally, the online ordering server 206 may comprise a transactional component 212 that processes the user's financial information. The transactional component enables the online ordering server 206 to obtain pertinent information from the user, healthcare provider and the user's insurance company to verify the prescription. The transactional component is also configured to carry out the payment of the order and informs the user if the prescription has been processed or if the financial transaction has failed.

Figure 8:
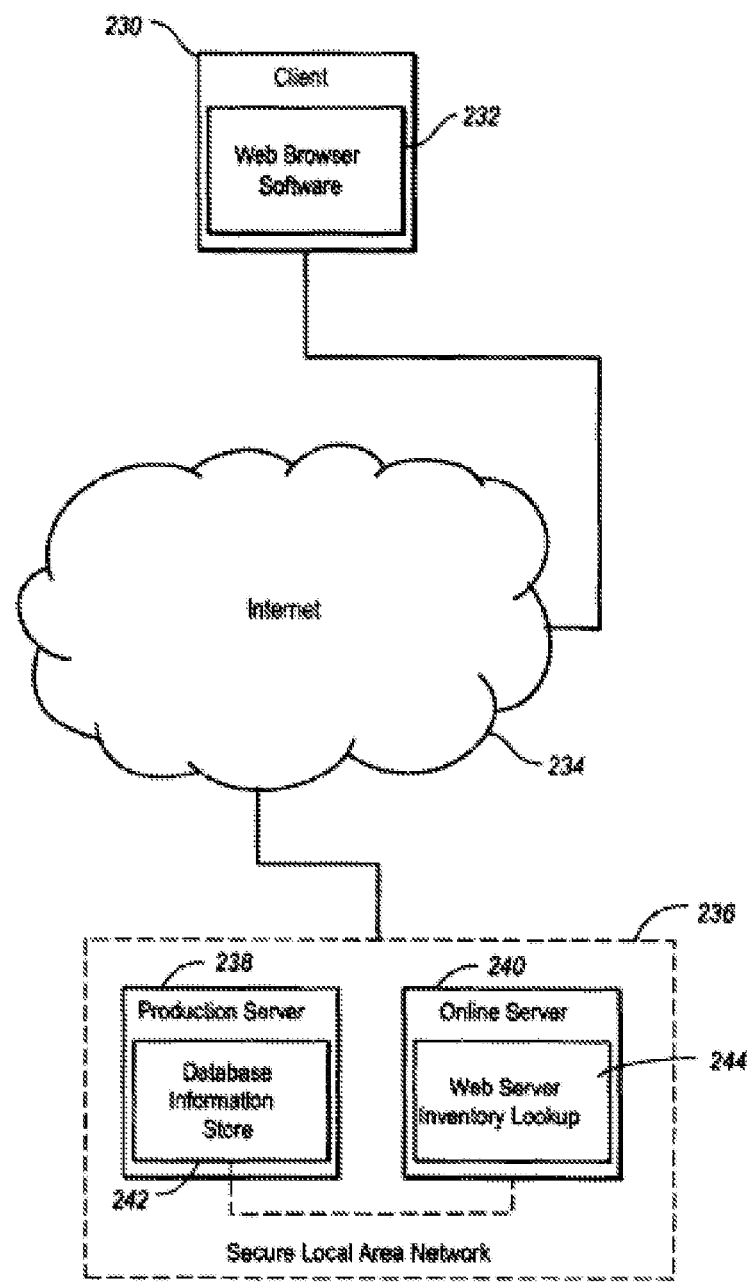
FIG. 8 is a block diagram of a client server architecture that outsources the filling of the multiple prescription order to a production facility.

Referring to FIG. 8, there is shown a block diagram of a simplified client server architecture in which the multiple prescription packaging is outsourced to the production facility. In this embodiment, the user orders tablets using a client 230 that is communicatively connected to a wide area network (WAN) such as the Internet 234. The client displays a user interface of an online application hosted on server 240. In some embodiments, the online application may be viewed using a standard web browser 232.

In some embodiments, production server 238 and online server 240 are part of secure LAN 236. The production server 238 is associated with managing the inventory in the production facility and comprises an inventory database module 242 that determines if the production facility can satisfy the client's prescription order. In some embodiments, a single server hosts both the ordering application and the database. The database may be on a server that is separate from the production server and the online server.

In the illustrative embodiment, the online server 240 comprises a web server inventory lookup module 244 that is operatively coupled to the inventory database module 242 and receives updates regarding the production facility's ability to satisfy the client's request.

In operation, the client 230 may access the production server 238 directly or through the illustrative online server 240 that may be associated with a separate on-line pharmacy, a physician, a health care provider, a health insurance provider, a school, a university or any other such entity. Additionally, physicians involved in the patient's care may utilize the Internet to generate a new prescription for the patient, or modify a previous prescription that may be stored on the production server 238.

Patient confidentiality may be preserved by using encryption technology and by requiring strong authentication. Using encryption technology such as Secure Sockets Layer (SSL) and Public Key Infrastructure (PKI), communications across the Internet 234 are kept secure. Illustrative embodiments may use available encryption tools such as Pretty Good Privacy (PGP), Open PGP and other available PKI encryption standards. Information stored on databases and servers may also be encrypted. Strong authentication may be obtained by asking the user for one or more unique identifiers such as date of birth (DOB), unique IP address, last 4 digits of a social security number, username, password, or any other such unique identifier.

Once the client 230 has been authenticated, the client is able to place a multiple prescription order using the ordering application. In one illustrative example, a pharmacist's on-line server communicates with the production server 238 and the inventory database 242. The pharmacist's on-line server makes a request to determine whether the production facility can satisfy the pharmacist's order. The inventory database 242 is accessed to determine if the prescription order may be filled. Once the pharmacist's online server has received confirmation that the prescription order can be filled, the online server relays this information back to the client's computer via the Internet.

By way of example and not of limitation, the illustrative production server 238 comprises software to access the drug interaction database to determine if there may be possible interactions between ordered tablets. The production server 238 also communicates the order to production facility computers which control the various systems and subsystems involved in producing the tablet assembly, including printers for labeling the lidstock on each individually sealed container with medication instructions such as date and time to take the tablets in each individual container. The production server 238 may also communicate to production facility computers which are connected to a printer for labeling an area of the sleeve portion of the tablet assembly, with end user information, drug information and expiration date(s) for the medication stored within the individual containers. It should be noted that vitamins and herbal supplements may also be stored together with prescription drugs.

Figure 9:
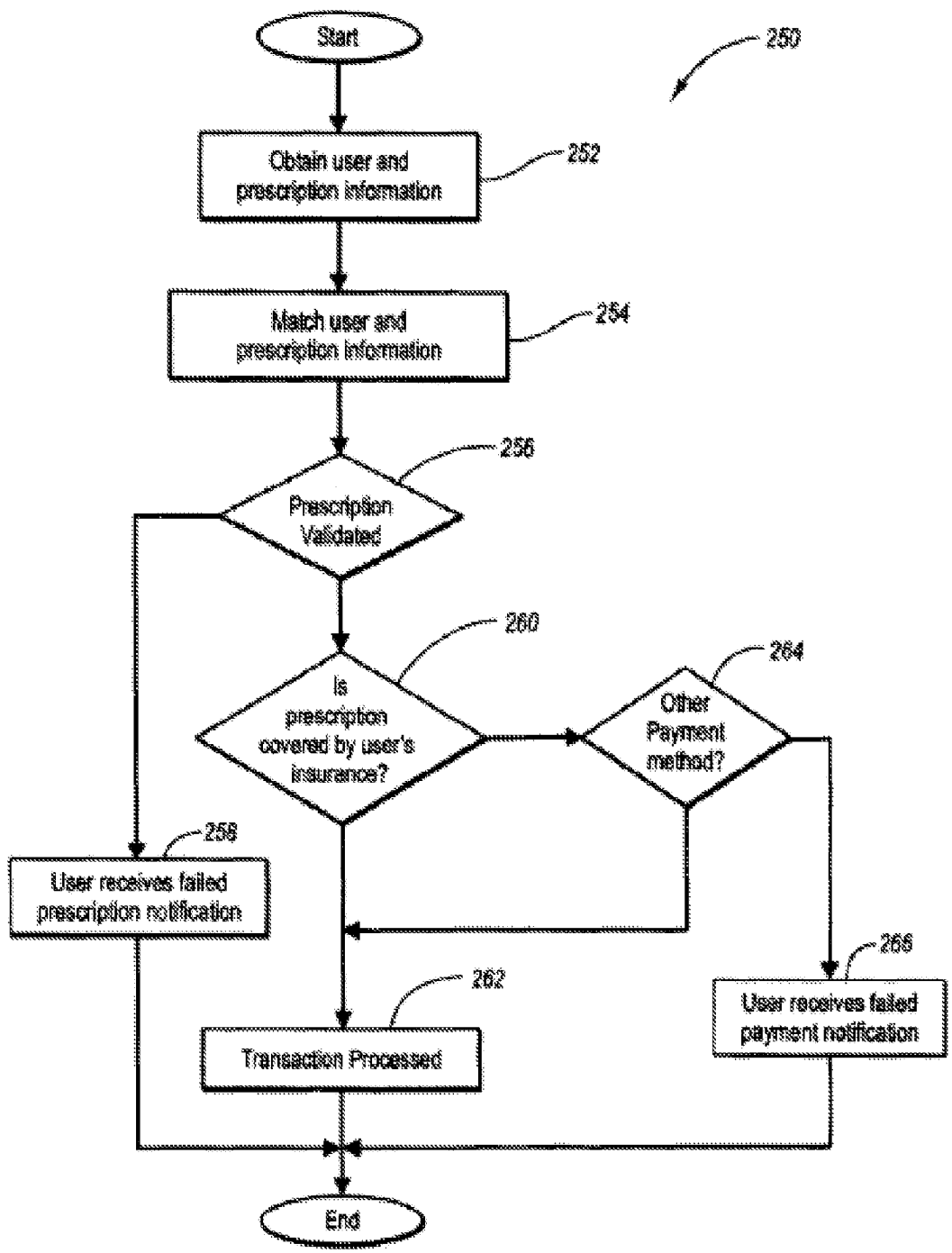
FIG. 9 is a flowchart showing a prescription validation process.

Referring now to FIG. 9, there is shown a flow chart of an illustrative prescription validation process 250. The prescription validation process is initiated at block 252 where user information and prescription order information is provided to either online ordering server 206 or online server 240. The method then proceeds to block 254 where user information is matched against the prescription order information.

At decision diamond 256, the prescription order is validated if user information and prescription information also match information stored on the online server. Additionally, the prescription may be validated after the online server communicates with another server such as the medical provider's server. Alternatively, the prescription order may be simply validated if the user information matches the prescription information. For example, if either the patient information or the prescription order information does not match the information stored on the online server, then the method proceeds to block 258 where the user receives a failed prescription notification. By way of example and not of limitation, an explanation may be provided by the online server, such as: the patient's personal information does not match the stored records, the prescription has expired, a physician's examination is required before filling the order, or the patient needs to wait for a specified period of time before the prescription order may be filled.

If the prescription order is successfully validated, the method proceeds to decision diamond 260 and determines if the prescription order is covered by the user's health insurance. As with prescription information, the insurance information for a specific user may be stored on a database associated with the online server of the production facility or the health insurance company's server may be queried by the online server via secured network about the accuracy of the user's insurance policy such as determining if the insured's policy is up-to-date. Additionally, information about the medications covered by the specific insurer may be queried, co-payment information, prescription drug policy, secondary insurance information, or any other such pertinent insurance information.

If the prescription order is paid for partially or fully by the user's health insurance, the method proceeds to process the transaction at block 262. A more detailed view of the transaction process 262 is provided below in FIG. 10.

The prescription order may not be covered, or may only be partially covered by the user's insurance and so the method proceeds to decision diamond 264 where alternative payment methods can be provided. By way of example and not of limitation, alternative payment methods include credit card, debit card, PayPal transactions, Electronic Fund Transfers, and other such methods for performing on-line transactions. If the alternative payment method can be processed, the method proceeds to block 262 where the transaction is processed. However, if the alternative payment method cannot be effectively processed, the method proceeds to block 266 where the user receives a failed payment notification.

Figure 10:
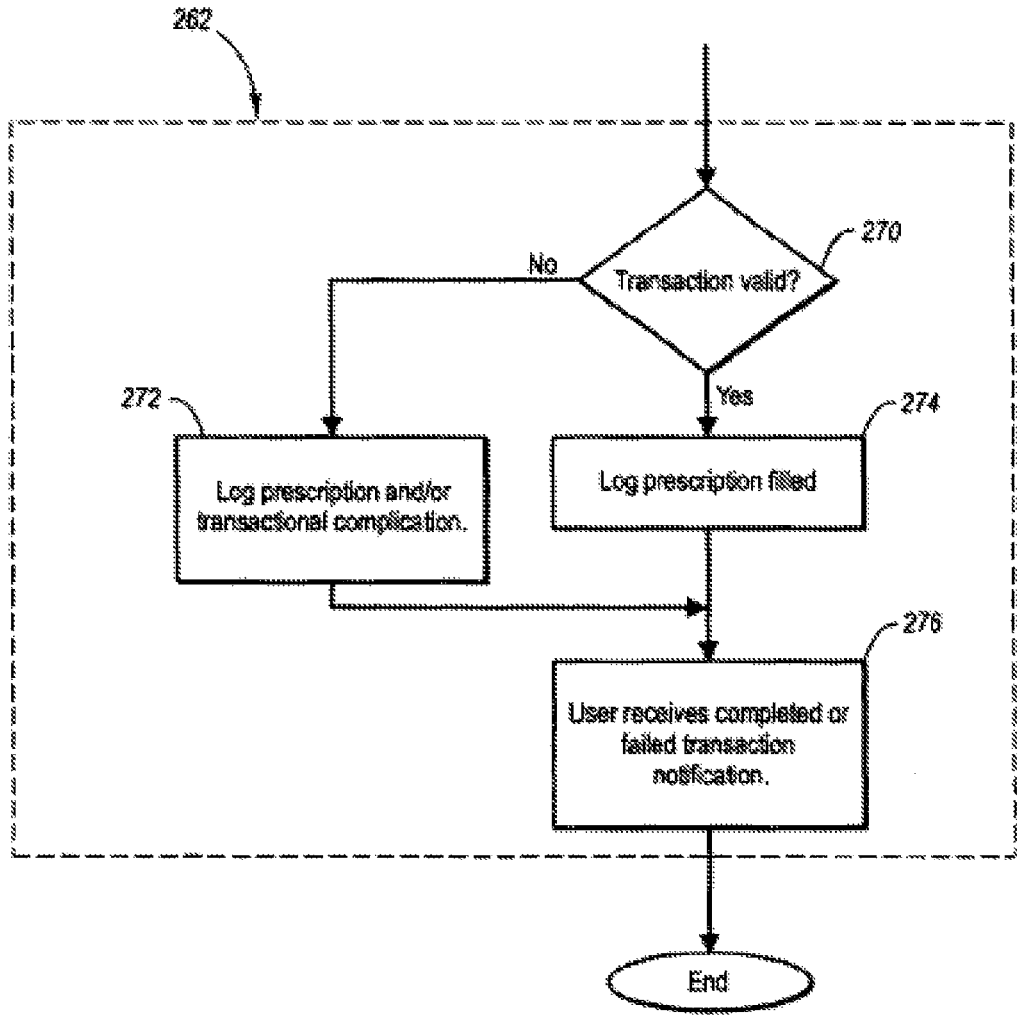
FIG. 10 is a flowchart showing a transaction being processed.

Referring to FIG. 10 there is shown an illustrative method for processing an illustrative transaction in block 262. At block 262, the online transaction is processed, which enables the online server to send confirmation that the illustrative prescription order has been filled. The method is initiated at decision diamond 270 where a determination is made concerning whether the transaction is valid. A transaction is valid when the information for payment of the multiple prescription order has been authenticated.

If a determination is made that the transaction is not a valid transaction, the method proceeds to block 272 where a log of either the prescription complication, transaction complication, or both is recorded. The prescription complication may arise because the production facility can not satisfy the order. The transactional complication may be caused by the payment method not being authenticated.

If the transaction is valid, the method proceeds to block 274 where the log indicates that prescription has been filled. The processing of the online transaction may also comprise confirming that the drugs requested are in the production facility's inventory and ready for dispensing. Inventory information may be stored on either the online server or the production server or on any other communicatively connected database or computer associated to the transaction component of the online server.

After determining whether the transaction is valid, the method proceeds to block 276 where the user receives a completed or failed transaction notification. In the illustrative example, the failed transaction notification comprises information explaining to the user that the transaction failed because an invalid credit card number was provided. If the transaction is determined to be valid, the prescription is logged as filled and the user receives a prescription completed notification via the network connection between the online server and the user's computer.

Figure 11:
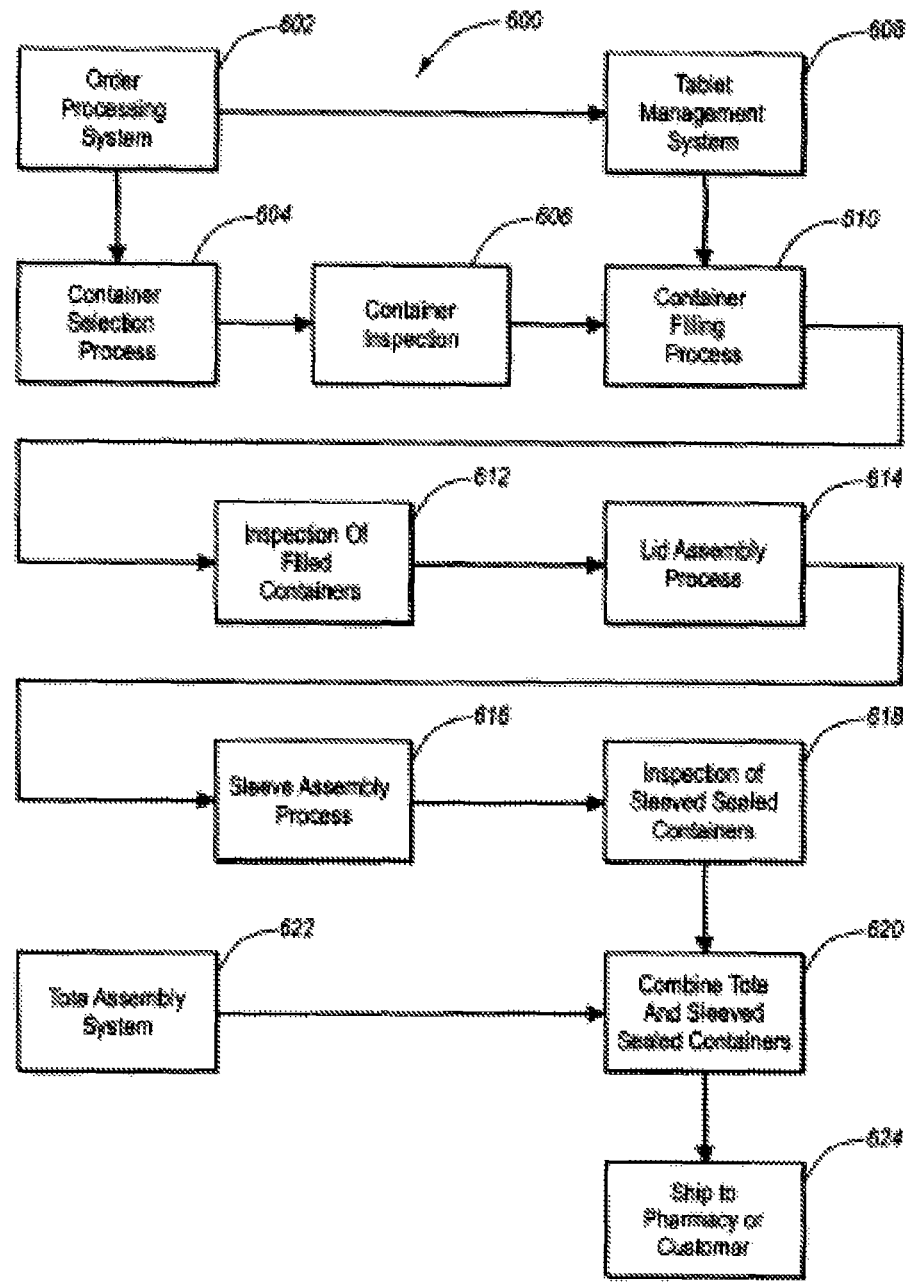
FIG. 11 is a flowchart showing the processes and systems used by a production facility to fill a prescription order.

Referring to FIG. 11, there is shown a flowchart of the production facility processes 600 used by an illustrative production facility to fill a prescription order. After receiving the prescription order in one of the illustrative system and/or methods described above, the order processing system 602 begins controlling the filling of the prescription order. By way of example and not of limitation, the ordering processing system 602 interfaces with an online server, production server, or both, and receives data that relates to the type of medication or tablet, and the type of multiple prescription container assembly that needs to be filled with the appropriate medications and/or tablets. The systems or methods for controlling production can be performed using a centralized control system or a distributed control system. Additionally, there may be instances where a combination of centralized and distributed control is optimal depending on design requirements and expectations.

The order processing system 602 is in communication with a tablet management system 608. The tablet management system 608 controls the tablets contained in the pill refill modules, which in turn are contained in multiple prescription containers. The tablet management system 608 also communicates when a refill module is not properly being filled.

The order processing system 602 also communicates with a container selection process 604. The container selection process 604 may receive an order for a particular container assembly from the user placing the order, e.g. pharmacist, caregiver, patient, etc. Alternatively, the container selection process 604 may receive a multiple prescription order lacking a container designation, in which case the appropriate container for filling the order must be selected. The container determination may be made in accordance with predefined parameters, e.g. less than 5 tablets require a small container, 6-10 tablets require a mid-size container, and 10-20 tablets require a large container.

After the container selection process 604, there is a container inspection process 606 during which inspection of the appropriate container is performed, to ensure that the appropriate container or substitute container has been selected. Additionally, the inspection process 606 may include identifying whether the container is broken or has some obstruction that may cause some difficulty to downstream systems and/or processes.

After the container inspection 606, the container filling process 610 is initiated. In an illustrative example, the container filling process 610 occurs by placing the selected container on a pallet or tote and moving the pallet or tote on a conveyer, which moves the pallet to the appropriate filling location so that the appropriate tablets may fill the container.

After filling the appropriate container with a plurality of medications and/or tablets, an inspection of the filled containers is performed at block 612. The inspection may be conducted by using X-ray detection, near infrared detection, robotic detection at visual wavelengths, or any other such technique that looks at color, shape, density, or other such parameter to determine if the appropriate container has been filled with the correct prescription. Thus, in certain instances, a visual inspection by a pharmacist may be satisfactory.

After inspection, the method proceeds to the lid assembly process 614 during which the lid is applied to the multiple prescription container. The sleeve is then applied at the sleeve assembly process in block 616. Alternatively, a cap may be placed on the sealed multiple prescription container, as described above. For purposes of this patent, the term "sleeved container" encompasses a multiple prescription container having a cap, unless otherwise indicated.

At block 618, the inspection of the sleeved sealed containers is conducted. This inspection at block 618 is performed after the multiple prescription container has been sealed. Note, the inspection at block 612 was conducted before sealing. The need for the second inspection described in block 618 is in case a tablet or medication fell out of the container or was mislabeled. Additionally, one of the tablets or medications may also have been broken or otherwise compromised. As stated above, the inspection may be conducted using a variety of different instruments including, but not limited to, robotic inspections at a visual wavelength, near IR, X-ray and any other detection means that can identify the type of tablets or medication in each container.

The method then proceeds to block 620 where the sleeved sealed container(s) are combined with printed materials in the tote. The printed materials may include labels as described in FIGS. 4-6 above. Additional materials may also be provided such as printed materials from pharmaceutical companies, medical providers, pharmacists, and other such entities. The printed materials are controlled by the tote assembly system 622. The printed materials may be generated at the production facility or may be shipped to the production facility or any combination thereof.

After combining the printed materials and the sleeved sealed multiple prescription containers, the combination is shipped to a pharmacy or customer as described by block 624.

Figure 12:
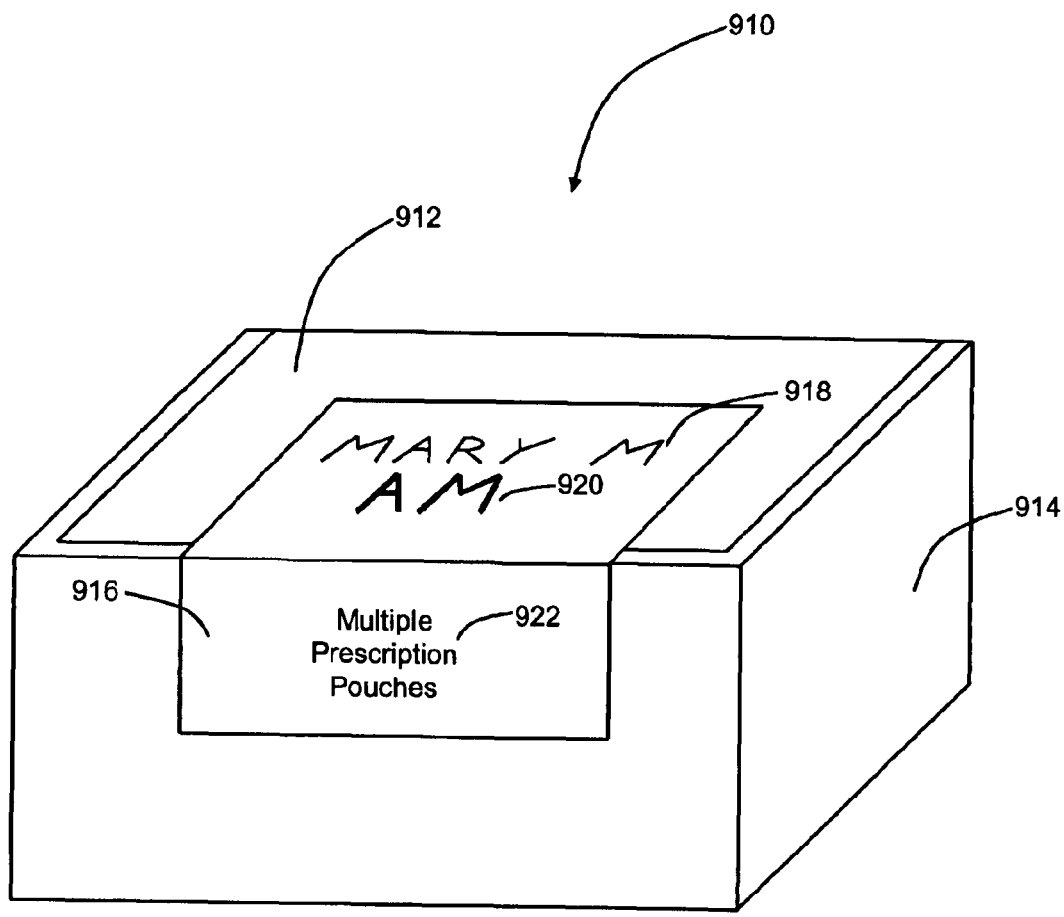
FIG. 12 shows a perspective view of an illustrative sealed outer box or "final package" for an alternative packaging assembly and apparatus.

Referring to FIG. 12, there is shown a perspective view of an illustrative sealed outer box or final package for a packaging assembly and apparatus. In this package, the illustrative sealed outer box or "final package" 910 comprises a lid 912 that is coupled to the back sidewall (not shown) of the outer box 910. The remaining sidewalls 914 abut the lid 912. An illustrative label 916 seals the outer box 910 by coupling the lid 912 with a front sidewall. The label 916 includes a plurality of information such as the patient name 918, e.g. Mary M. Additionally, the label may include an illustrative dosing interval 920, e.g. A.M. (morning intervals for taking the medications), and additional information 922 about the different medications within the outer box 910. The additional information 922 may include the type of prescriptions within the box, a serial number associated with the patient, the prescribing physician, the pharmacy that filled the prescription, the dosage period, a bar code, or any other such information that may be placed on the label. To open the outer box 910, a patient or caregiver simply breaks the label 916 to access the components within the outer box 910.

The final package 910 comprises a plurality of secondary containers as described below. Additionally, the final package may comprise package inserts and PRN medications as described in further detail below.

Figure 13:
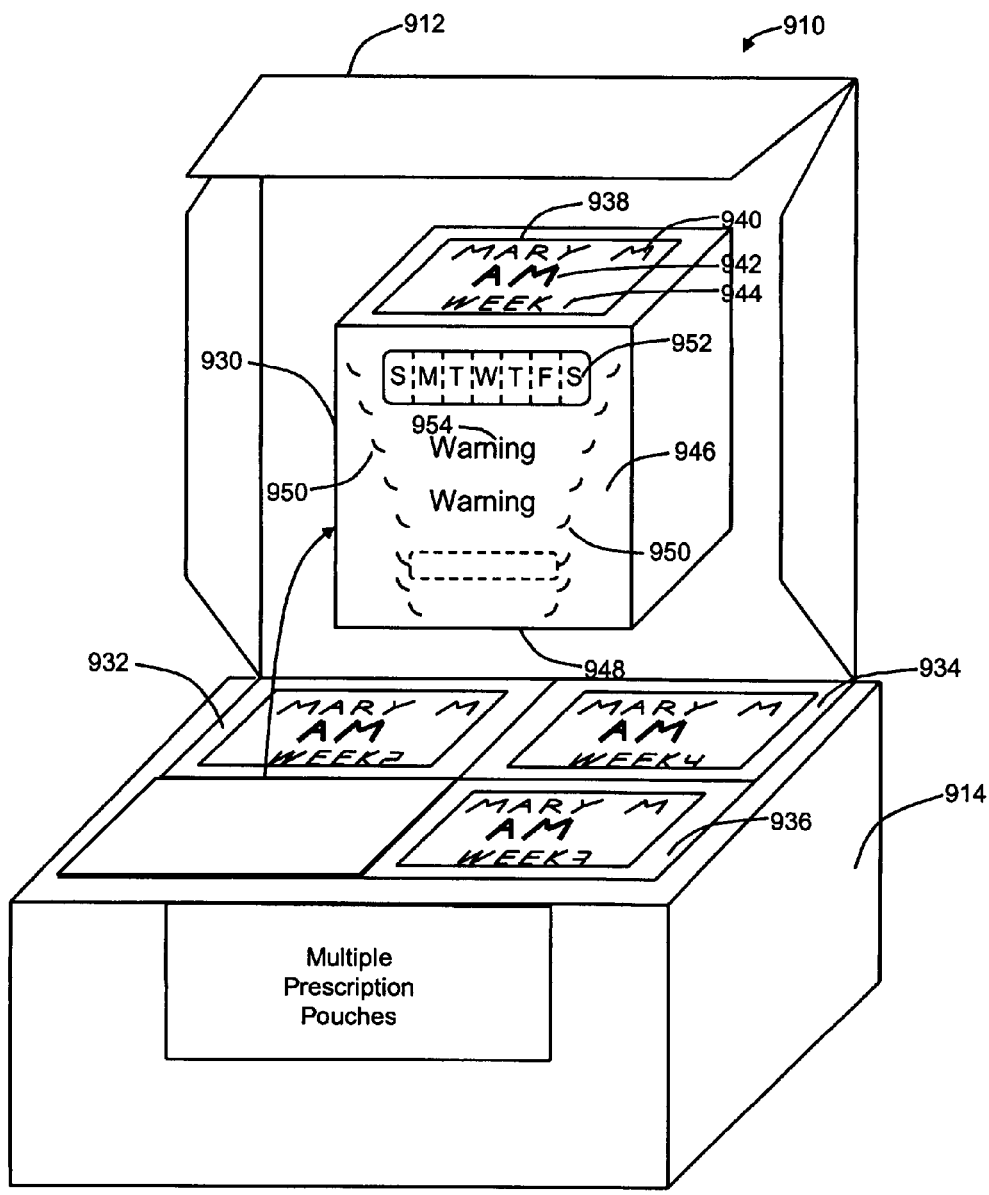
FIG. 13 shows the opened final package and a plurality of sealed containers or "secondary containers" of FIG. 12.

Referring to FIG. 13 there is shown the opened final package of FIG. 12, and a plurality of sealed containers or "secondary containers" within the outer box 910. The illustrative final package 910 provides medications for the 28-day dosing period. Within the illustrative outer box 910 there are four secondary containers 930, 932, 934, and 936. The size of each secondary container depends on the quantity and type of tablets held by each container. Each secondary container is initially sealed, and provides medications for a 7-day dosing period. Each secondary container comprises a plurality of pouches. Additionally, the container is configured to receive labeling information as described herein.

The first secondary container 930 is shown after having been taken out of the final package 910. The container 930 comprises an illustrative label 938 that provides information such as the patient name 940, e.g. Mary M, the dosing interval 942, and additional information 944, e.g. "week 1" dosing period. Furthermore, the additional information 944 may include the type of prescriptions within the container, a serial number associated with the patient, the prescribing physician, the pharmacy that filled the prescription, the dosage period, or any other such information that may be placed on the label. The first primary container 930 is initially sealed and has a front face 946, which can be torn open by lifting the bottom lip 948, and tearing the front face along the perforations 950. The illustrative front face also comprises a plurality of tear-off tabs 952 or removable elements, e.g. circular perforations, for each day of the week during the 7-day dosing period, in which the tear-off tabs are seen through a cut-out. Additional labels or printed materials can also be provided on the front face 946, such as "warning" information, or emergency contact information, or any other text based or Braille information. Those of ordinary skill in the art shall appreciate that the description of the illustrative first secondary container 930 also applies to the remaining containers 932, 934, and 936.

Figure 14:
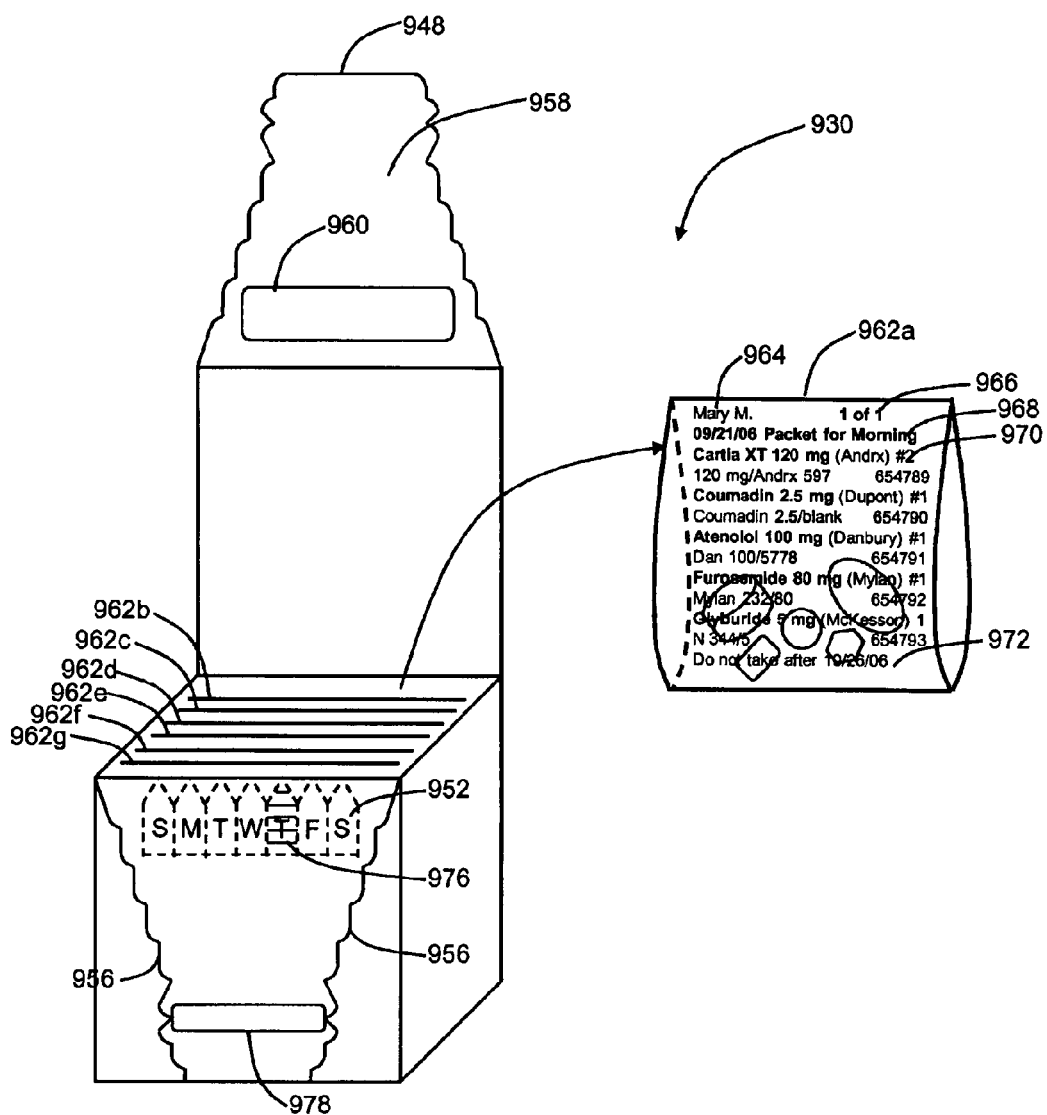
FIG. 14 shows a perspective view of an opened secondary container housing a plurality of pouches.

Referring to FIG. 14, there is shown a perspective view of an opened secondary container housing a plurality of pouches. In the illustrative embodiment, the opened container 930 is opened by lifting the bottom lip 948 and tearing the front face along the perforations resulting in perforated edges 956 on the front face of the container 930. The resulting container lid 958 is fixedly coupled to the back sidewall of the container. The container lid 958 comprises an opening or cutout 960 that serves as a window to view the tear-off tabs 952.

Within the container 930 are a plurality of pouches 962a through 962g, e.g. a seven-day supply of medications. An illustrative preliminary package 962a is lifted from the container. The illustrative pouch 962a comprises a plurality of printed text that may include the patient's name 964, a number of pouches 966 that are to be consumed, a date and time 968 associated with consuming the contents within the packet, tablet information 970 such as name of the particular prescribed medications, dosage concentration, lot number, and other such information. Additionally, an expiration date 972 is provided. In the illustrative example, the pouch is transparent and the medications within the pouch are visible for a variety of reasons including quality control. After the preliminary package is consumed, the patient or caregiver may remove one of the applicable tear-off tabs 952. By way of example and not of limitation, the date that the pouch is consumed is Sep. 21, 2006, which falls on Thursday. The patient or caregiver may remove the Thursday tab 976 so that the patient or caregiver can quickly determine that the medications were taken on specific prescribed days. After consuming the medication in the packet 962a, the container 930 is closed by putting the bottom lip 948 of the container lid 958 into the slot 978 on the front face of container 930. The secondary container may also contain additional labeling information on the underside of the container lid 958 as shown in FIG. 15A, which is described in further detail below.

Figure 15A:
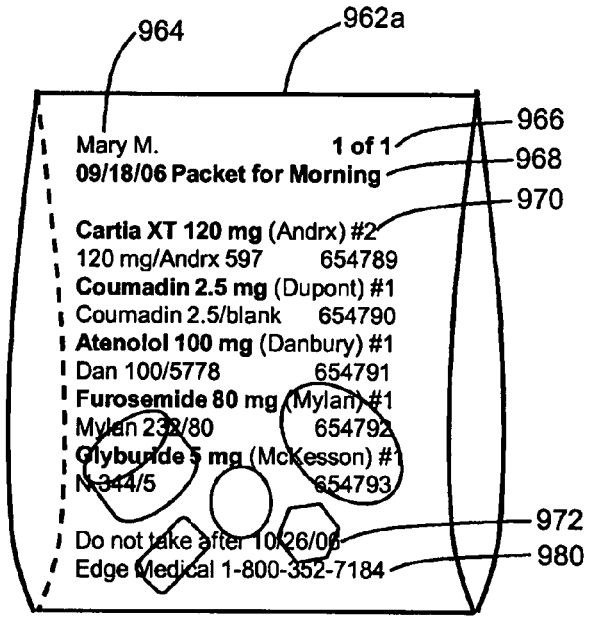
FIG. 15A shows an exploded view of an illustrative sealed pouch or "preliminary package" comprising a plurality of tablets associated with different medications.

Referring to FIG. 15A there is shown an exploded view of the illustrative sealed preliminary package 962a comprising a plurality of tablets associated with different medications. The preliminary package provides a more detailed view of the transparent pouch or packet having a plurality of tablets associated with different medications. The labeling or printing on the pouch 962a is similar to the labeling shown in FIG. 14, and comprises printed text that may include the patient's name 964, a number of pouches 966 that are to be consumed during a particular dosing interval, a date and time 968 associated with consuming the contents within the preliminary package, e.g. pouch. The illustrative tablet information 970 includes the name of particular prescribed medications, the generic or trademarked name, manufacturer, the concentration associated with the tablet, the lot number, and other such information that is associated with the tablets or medications. For medications that must be consumed within a particular period of time, an "expiration" date 972 may also be provided. Furthermore, contact information 980 may also be provided, so that additional information associated with the tablets or medications can be obtained. For example, an order may have to be refilled so pharmacy information may also be located on the pouch.

Figure 15B:
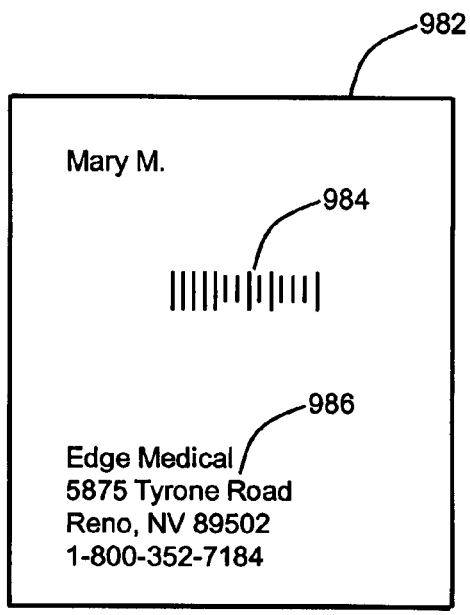
FIG. 15B shows a first illustrative label that is associated with a secondary container.

Referring to FIG. 15B there is shown an additional label that is associated with illustrative secondary container in FIG. 15A. The additional label 982 may be an empty pouch that has additional information that could not be printed on the pouch 962a. The additional information may include a bar code 984 for tracking the medications within the pouch. Other information such as the dispensing pharmacy 986 may also be provided. Furthermore, additional medical information may also be provided such as side effects and warnings associated with the tablets may be provided on the label 982.

Figure 16A:
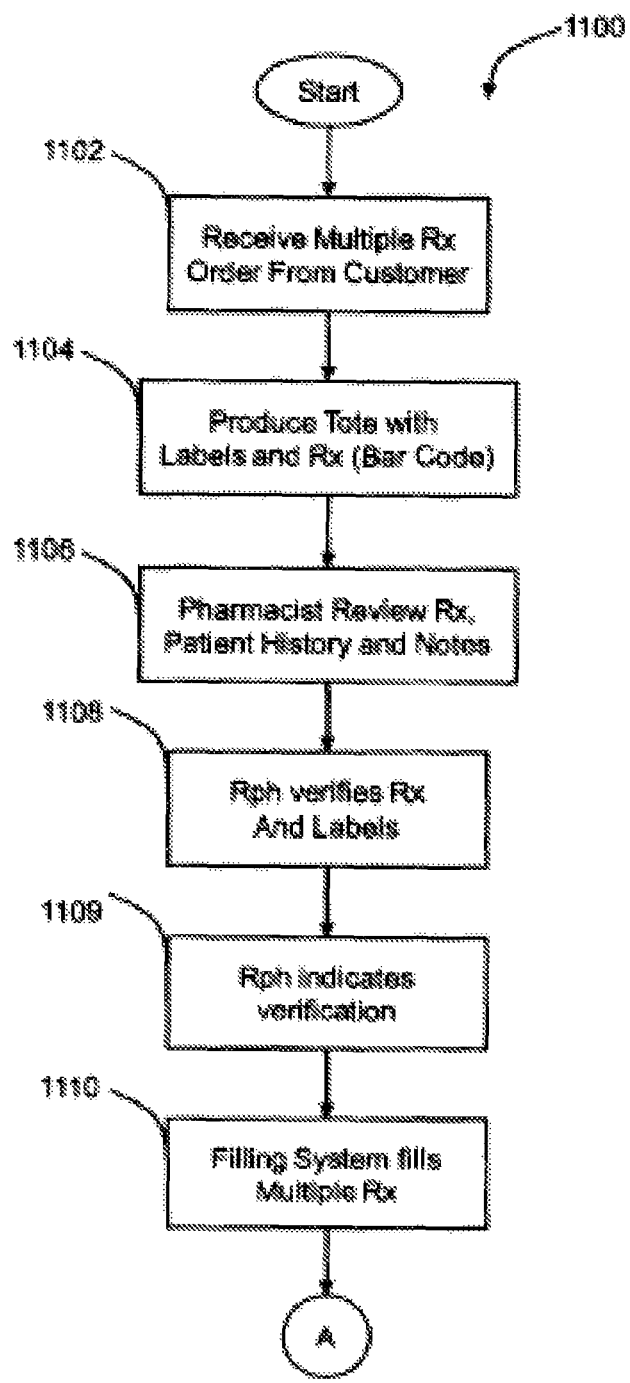
FIGS. 16A-16C are an illustrative flowchart showing a method for the assembly of a secondary container and a final package.
Figure 16B:
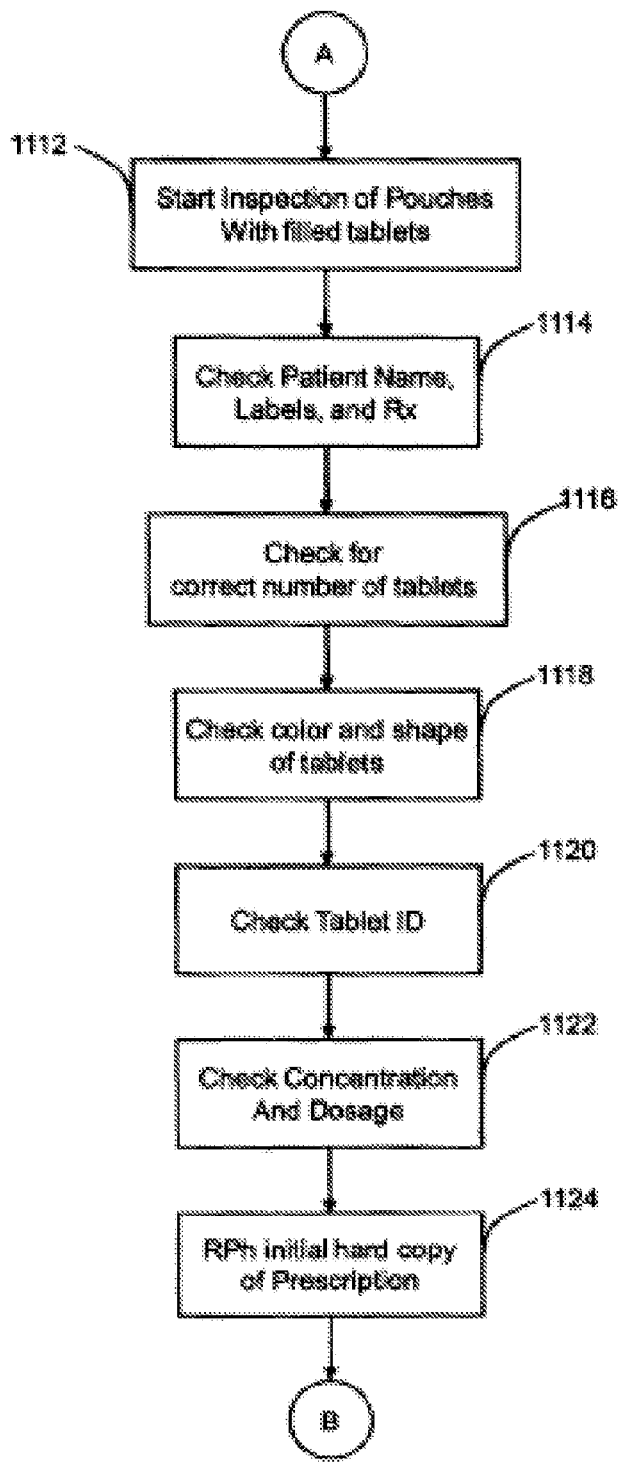
Figure 16C:
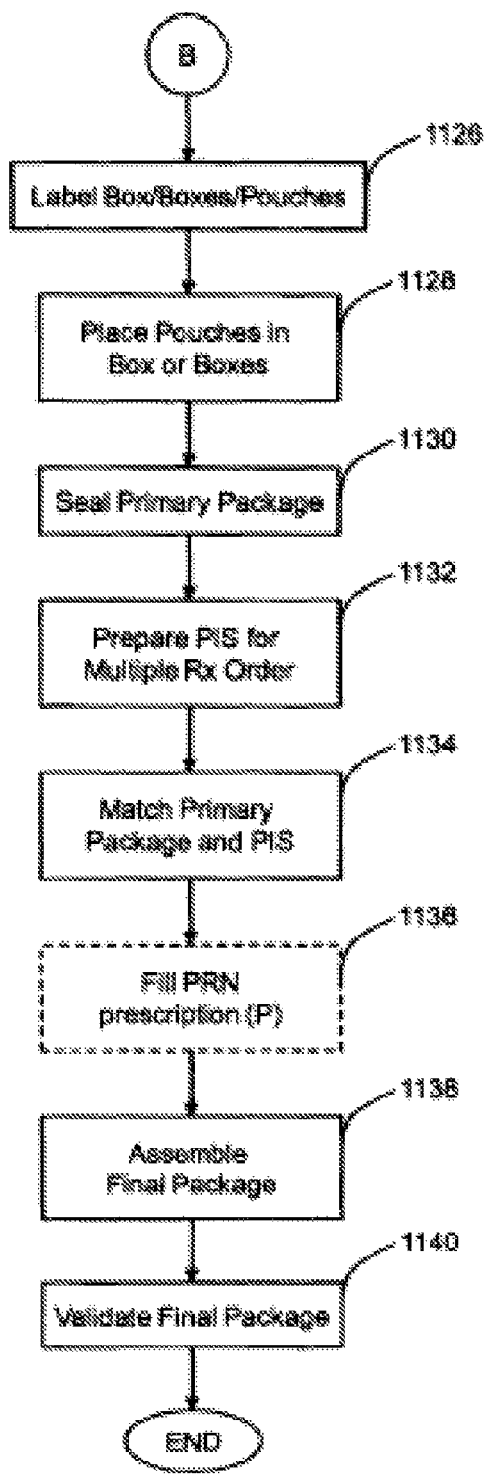

Referring to FIGS. 16A-16C, there is shown an illustrative flowchart for the assembly of the final package, the secondary container and a multiple prescription pouch. A multiple prescription pouch refers to a package that combines a plurality of different tablets into a single pouch. A multiple prescription order is required to generate a multiple prescription package. The pouch may refer to a pouch, a cup, a matchbook, a blister pack, or any other similar packaging means that can hold a plurality of different medications. The secondary container also comprises a container configured to hold a plurality of pouches, which hold a plurality of different tablets. In one embodiment, the secondary container is combined with package inserts, and possibly PRN (to be taken as needed) medications to produce a "final package." The final package is ready for pick-up or shipping.

A multiple prescription order comprises a plurality of medications that are different from one another. Additionally, the multiple prescription order may indicate the frequency with which the medications are to be consumed. Furthermore, the prescription may indicate the particular time interval that each medication should be taken, i.e. morning, noon, evening, and bedtime.

The description provided herein describes systems, apparatus, labeling techniques, and methods that can be used to take a preliminary package and convert this to a multiple prescription package or secondary container, which can then be integrated with package inserts to produce a final package that is ready for pick-up or delivery. A method for assembling the multiple prescription package that can be easily transported and administered is also described. The final package is properly validated to assure that the appropriate medications are in the secondary container. Additionally, the final package accommodates package inserts. Furthermore, a method for verifying the prescription, the preliminary package, and the secondary container is described.

The illustrative flowchart 1100 is initiated in FIG. 16A at block 1102 where a multiple prescription order is received from a customer. After receiving the prescription order, a technician may proceed to input the customer information into a graphical user interface (GUI) for a pharmacy management program such as PharmaServ, which is a pharmacy management system available by McKesson. The Pharmaserv pharmacy management system performs operations including prescription processing, claims adjudication, inventory management, and integration with automation and workflow. Additionally, the technician may also scan the prescription order to generate a digitized copy of the prescription order.

In one embodiment, after inputting the customer information into the pharmacy management system, the pharmacy management system performs the claims adjudication process and generates a hard copy of the prescription, and prints out any notes received from the patient. A variety of labels may be printed separately using a personal computer and printer. The illustrative labels may be conventional labels having an adhesive backing affixed to wax paper. The illustrative labels may also be fastened using other methods such as stapling, taping, or other such fastening means. The thickness of the illustrative labels also varies. In another embodiment, the prescription, labels and notes are associated with a particular bar code or other identification means, e.g. RFID that is associated with the prescription order. The hard copy of the prescription, the plurality of labels, and any notes are placed into a tote. The process of producing a tote having the labels, prescription, and bar code is shown at block 1104.

In the illustrative flowchart, the pharmacist proceeds to block 1106 where the pharmacist reviews the patient history, the prescriptions, and the notes associated with the patient. In the illustrative embodiment, the pharmacist keys in the patient information from the hard copy of the prescription that is within the tote into the pharmacy management program. Additionally, the patient history that is stored in the pharmacy management program is reviewed by the pharmacist. Furthermore, the pharmacist verifies each new prescription or existing prescription associated with the patient. Further still, the pharmacist checks to see if there are any patient notes that require taking action.

After reviewing the prescription, patient history and notes associated with the patient, the prescription and labels are verified by the pharmacist at block 1108. The verification process may comprise determining that the patient's name and date of birth are correct on each label and that the correct date has been provided. Additionally, the drug strength, quantity, and refill status may be checked. The pharmacist may also determine whether the medical professional prescribing the medication is correct and has provided a valid signature. Furthermore, in the illustrative embodiment, the pharmacist may proceed to determine whether a "dispense as written" (DAW) designation is correct. The DAW designation limits the pharmacist to dispensing a prescription according to a specific provision authorized by the patient's health plan. If the prescription and labels cannot be properly verified, the pharmacist will attempt to correct the error. However, if any error identified in the verification process cannot be corrected, the prescription and labels are rejected.

In another embodiment, an additional bar code or other identification means is used to track and verify the prescription and labels. The illustrative bar code or other identification means may be associated with the name of the patient, the patient's date of birth, the prescription, the drugs or medications, the drug strength, the quantity, the refill status, the medical professional prescribing the medication, the DAW designation, or any combination thereof.

Figure 17A:
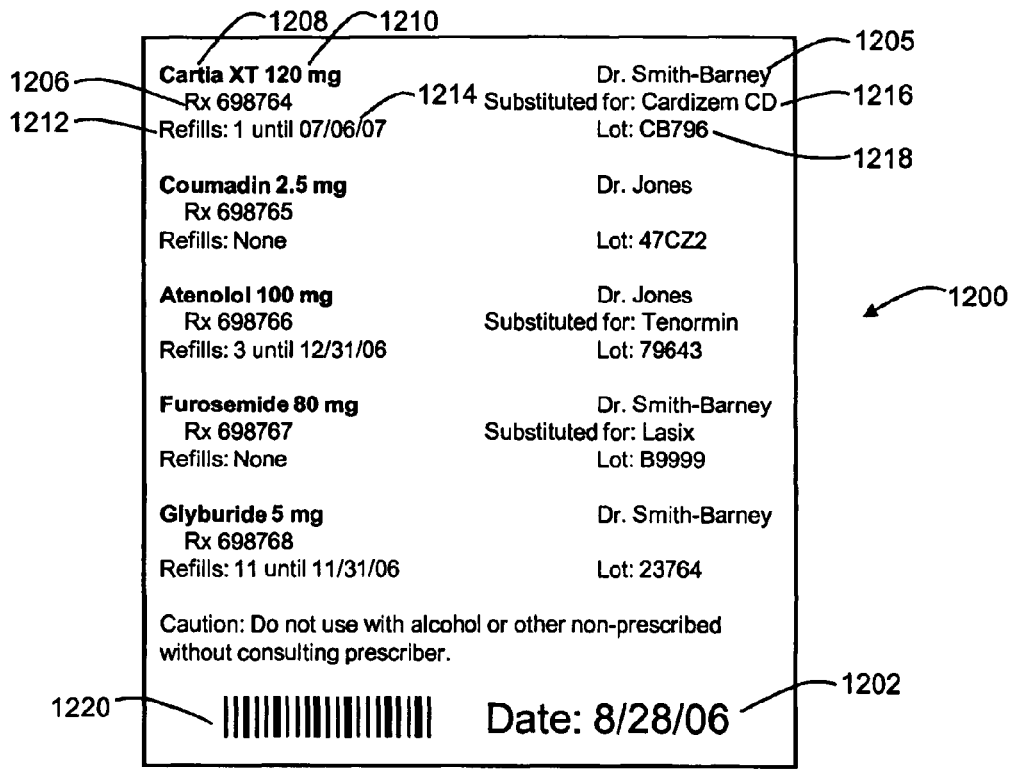
FIGS. 17A-17B depict two illustrative labels applied to a secondary container.
Figure 17B:
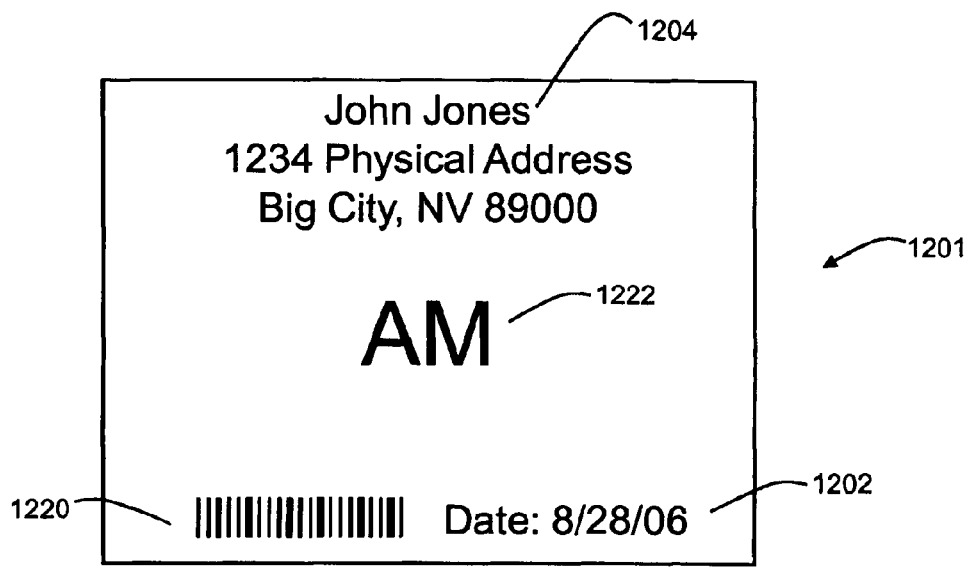

The verification of the labels is not a trivial process. Referring now to FIGS. 17A-B, there are shown two illustrative labels 1200 and 1201 that may be placed on an illustrative container that receives a plurality of filled multiple prescription order. By way of example and not of limitation, the labels may show: the date 1202; the patient's name and address 1204; the name of the prescribing physician 1205; the prescription serial number of the practitioner who filled the prescription (not shown); the prescription number 1206; the proprietary or generic name of the drug or medicine 1208 as written by the prescribing physician; the concentration 1210 of the associated drug; the number of dosage units; specific directions for use given by the prescribing practitioner; the expiration date of the effectiveness of the drug or medicine that is dispensed; the strength of the drug or medicine; the appropriate label warnings; the number of refills 1212; expiration date for refills 1214; substitutions 1216; the lot number 1218; identification means such as a bar code 1220; the interval 1222 for consuming medication, e.g. morning, noon, afternoon, or bedtime; or any combination thereof. Additionally, the label may include a bar code and a date that can be used for tracking and verification purposes.

In the illustrative embodiment the label 1200 is applied to the inside cover 980 of the illustrative secondary container 930 described above in FIG. 14. The second label 1201 is applied to the top surface of the secondary container 930.

Returning to FIG. 16A, after the pharmacist verifies the prescription and label at block 1108, the pharmacist indicates that the prescription has been validated in block 1109. To indicate that the prescription has been verified and accepted, a label from the tote is affixed the back of the prescription hard copy. The pharmacist then proceeds to initial the hard copy of each prescription, which is returned to the tote for later inspection.

The verified prescription is then released and is forwarded to the filling system as represented by block 1110. By way of example and not of limitation, the filling system is a McKesson PACMED high-speed packager. The illustrative filling system is configured to generate a preliminary package, which is a pouch having a plurality of different medications. For purposes of this description the terms preliminary package and pouch are used interchangeably. Alternative filling systems as described above may also be used. Each pouch may receive a bar code, medication data, patient data and order data on the exterior of the pouch. Additionally, the illustrative filling system may be configured to apply the bar-code for pouch packaging purposes during the filling process. The output pouches generated by the filling system are then placed in the tote having the labels described above.

The method then proceeds to block 1112 shown in FIG. 16B, where an inspection of the illustrative filled pouches and the associated labels that are in the tote is initiated. The inspection of the pouches is initiated at block 1114 and comprises verifying or checking the patient's name on the pouches, and checking that the name on the pouches matches the name on the labels, and matches the hard copy of the prescription. In the additional embodiment, the bar code or identification means may also be scanned to verify that the correct pouches and labels are associated with the correct prescription.

If the patient's name matches, a visual inspection of each pouch may be performed. In the illustrative embodiment, the preliminary package or pouches are transparent and the visual inspection may include validating that the correct quantity of tablets is in the pouch as shown in block 1116. The inspection may then proceed to block 1118 where the color and shape of the tablets are also visually inspected. The visual inspection may then proceed to block 1120 where the tablet ID printed on the pouch is compared to the tablet ID on the tablet itself. At block 1122, the inspection process may also comprise verifying the concentration or dosage of each tablet within the pouch by checking the markings on the table. Thus, the correct quantity of tablets is verified, the type of medications within the pouch is verified, and the concentration or dosage is also verified.

The pharmacist may then proceed to block 1124 where each hard copy of the prescriptions is initialed by the registered pharmacist. The initialed or signed hard copy is filed and retained for at least two years. The tote having the preliminary packages and labels then proceeds to a boxing station.

Referring now to FIG. 16C, at block 1126, the tote having the labels and preliminary packages are received at the boxing station, and the labels are applied to one or more boxes. Additionally, the appropriate labels are also attached to the shipping container. At a minimum, the labeling that is applied to both the pouches and the container will need to comply with regulatory requirements for that particular jurisdiction. Although each pouch has a surface that can receive written text, the size of the pouch limits the available area for receiving text. Therefore, to comply with regulatory requirements additional information beyond that which can be placed on each pouch may be required. This additional information can be applied on another label, such as label 1200 described above. Label 1200 may then be applied to an illustrative container that is similar to the containers described above. The label may be placed on the inside cover of the illustrative container.

In another illustrative embodiment, another corresponding label is also applied to each of the pouches having the different medications. This additional labeling may be required to comply with regulatory labeling requirements. Furthermore, the additional labeling may be used for a particular patient group that may have special requirements. For example, the pouches may have to be adapted for usage by arthritic patients, blind patients, or other patients having special needs.

For example, for an arthritic patient group, the pouches may be quite difficult to open, and so the additional corresponding label is applied to the preliminary package to ease the process of opening the pouch. This additional label may be composed of a stiff paper backing and may have a notch with perforations to ease the tearing of the label and the underlying pouch material. For a blind patient group, the blind patients may be unable to distinguish one pouch from another, or be unable to tell when to consume the appropriate medications. Thus, the labeling for a blind patient group may require the use of Braille lettering or other encoding schemes that would allow a blind person to distinguish between preliminary packages or pouches and intervals for consuming their medication.

At block 1128, the preliminary packages are loaded into the outer box or boxes to create a "secondary container." The secondary container complies with the regulatory labeling and distribution requirements. In the illustrative example, the secondary container comprises a plurality of pouches that are placed within a container. By way of example and not of limitation, there may be a seven-day supply of medications within each container. The container is configured to accommodate a seven-day supply of medication. In another embodiment, a container may be configured to accommodate a 28-day supply of medication. As described previously, the container is also configured to receive a label that indicates the time of day or interval during which the medications within the pouch are to be consumed, e.g. morning, noon, evening, or bedtime.

At block 1130, the secondary container is sealed or glued. The illustrative secondary container comprises a plurality of preliminary packages and a container. For the illustrative secondary container there is a label on the exterior of the container that indicates the name of the patient and the interval when the patient should consume the medication, e.g. AM or morning. After sealing the secondary container, the secondary container is inspected to ensure that the appropriate labeling information is on the exterior of the secondary container. In the additional illustrative embodiment, the bar code on the container may be recorded and a database may be used to track that the container has been sealed. The inspection comprises making sure that the necessary label information is on the outside of the package.

At block 1132, the package insert or inserts (PIS) are prepared for the multiple prescription order. The package inserts have detailed information about indications, warnings, precautions, side effects, dosage, administration, and clinical pharmacology. The package inserts may also include summaries of the various medications being taken, and summaries of the side effects, and the associated administration. Although the package inserts are written primarily for a physician and pharmacist, the package inserts may be simplified so that they are easier to understand. In the illustrative embodiment, the package insert is associated with the secondary container and put into the final package, as described in block 1134. The package insert is configured to be distinguishable from other package inserts associated with another patient. Thus, the package insert is associated with all the medications in the secondary container. The package insert may also comprise a variety of different identification means such as the name of the patient, a bar code or any other such identification means. In the additional embodiment, the package insert is also configured to comprise a bar code to ensure that the correct package insert is associated with the corresponding prescription. Alternatively, the package insert may be combined with the secondary container so that the secondary container comprises a plurality of pouches, the package insert, and the outer box. The package insert should not be confused with the labels that are applied to either the container or to the pouches themselves.

At block 1136, the PRN prescription is filled. In a majority of cases, PRN prescriptions will not be filled; however, PRN prescriptions do account for a substantial number of prescription orders. PRN prescriptions are consumed on an as needed basis. The acronym PRN refers to dosage of prescribed medication that is not scheduled and for which administration is left to the caregiver or the patient's prerogative. PRN is the acronym for "pro re nata" that is commonly used to mean "as needed." Most often PRN medications are analgesics such as Tylenol®, laxatives, sleeping aids, and similar medications. In the additional embodiment, the bar code described previously may also be associated with the PRN prescription.

At block 1138, the final package is assembled. The final package comprises the secondary container and the package inserts. In certain instances the final package also comprises the PRN medications. The final package may also require shipping labels or other such labels indicating that the final package is ready for pick-up.

The method then proceeds to block 1140 where the final package is validated. The final package validation may include checking the events associated with the assembly of the final package. Therefore, the validation process may comprise checking to see if a pharmacist reviewed the prescription and labels, confirming that each pouch was checked after being filled, checking the method used to confirm the correct medications were in the pouch, confirming that a pharmacist had initialed the prescription after the prescription was filled, confirming that each tote has no labels, confirming that each container was sealed, checking to see that a PIS was generated, and that the PRN was filled, or any combination thereof. Thus, the validation process evaluates each of the process steps and determines whether or not each process step was performed. In the additional embodiment that comprises the bar code, the scanning or identification of the bar code at each process step may be required. After the final package is validated, the final package is released and is ready for pick-up or shipping.

In summary, the foregoing description is directed, in broad terms, to a multiple tablet ordering system and method, whereby a user (e.g., a pharmacist, a patient, a user, a customer, etc.) may place one or more multiple (or single) tablet orders. A multiple tablet order is an order for two or more tablets, which may be different or the same, and which are to be consumed at approximately the same time.

The system may operate by way of a network, and it may comprise, among other things, a client computer, an ordering server, and a production facility server. Ordering via an ordering interface on the client computer, a user may enter a plurality of prescriptions, all of which must be filled. An automatic filling machine may receive instructions (by way of a production facility server) for packaging a user's prescription medications in one or more multiple tablet containers (also referred to as preliminary packages or pouches). Each multiple tablet container holds a multiple (or single) tablet order. The filling machine may additionally generate a plurality of labels for attachment to each multiple tablet container, as well as to a larger container (i.e., a secondary container), which may hold or secure a plurality of multiple tablet containers. The information printed on the label may comprise a user's name, the date and time at which a particular multiple tablet container should be opened and its medications consumed, images of the tablets inside each multiple tablet container, the names of the tablets inside each multiple tablet container and their respective quantities, and a variety of other information, as set forth more fully above.

With regard to the ordering interface, a first embodiment is presented at FIG. 18A-22 below.

Figure 18A:
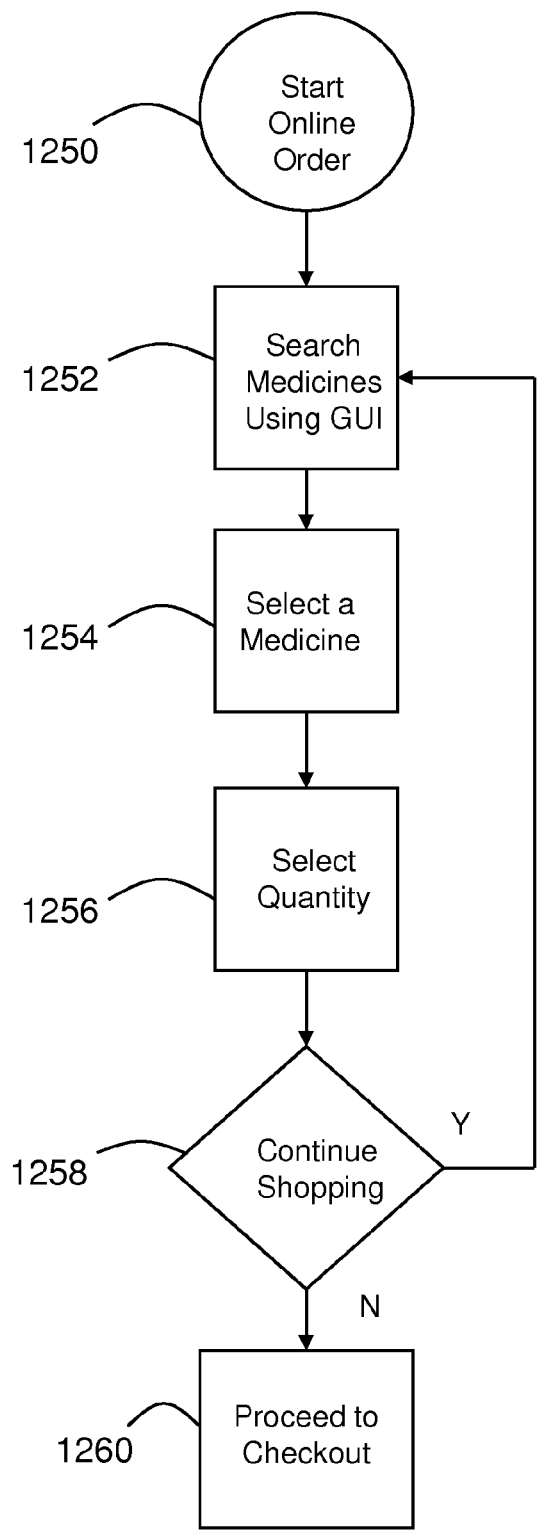
FIG. 18A shows an illustrative flowchart showing a method for placing a multiple tablet order online using a graphical user interface.
Figure 18B:
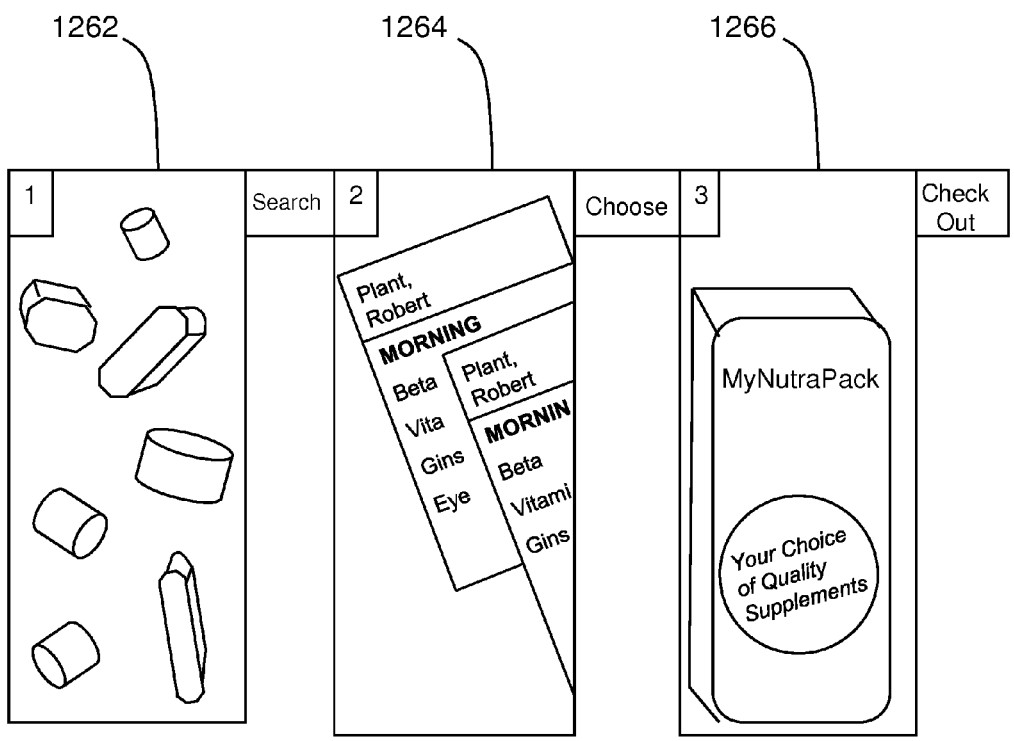
FIG. 18B shows an online ordering process.

Referring to FIG. 18A, a method for ordering tablets with an ordering application is presented. Broadly, the method permits a user to specify the number of tablets he would like to receive, or has been prescribed to receive, or is prescribing, for each dosing interval. The ordering application may be a web application accessed over a network such as the Internet. At step 1250, a user (e.g., a patient, caregiver, pharmacist, or physician) begins the online ordering process by opening a web browser which loads the ordering interface. As depicted in FIG. 18B, a simplified illustration outlining the online ordering process may initially appear. The simplified illustration may include a first illustration 1262 representing a step in which the user searches for medications, a second illustration 1264 representing a step in which the user selects one or more medications, and a third illustration 1266 representing a step in which the user checks out of the online store.

Returning to FIG. 18A, at block 1252, the user searches for one or more medications. The search may be of one or more lists of available medications. Alternatively, the user may conduct a string search for a desired medication.

Figure 19:
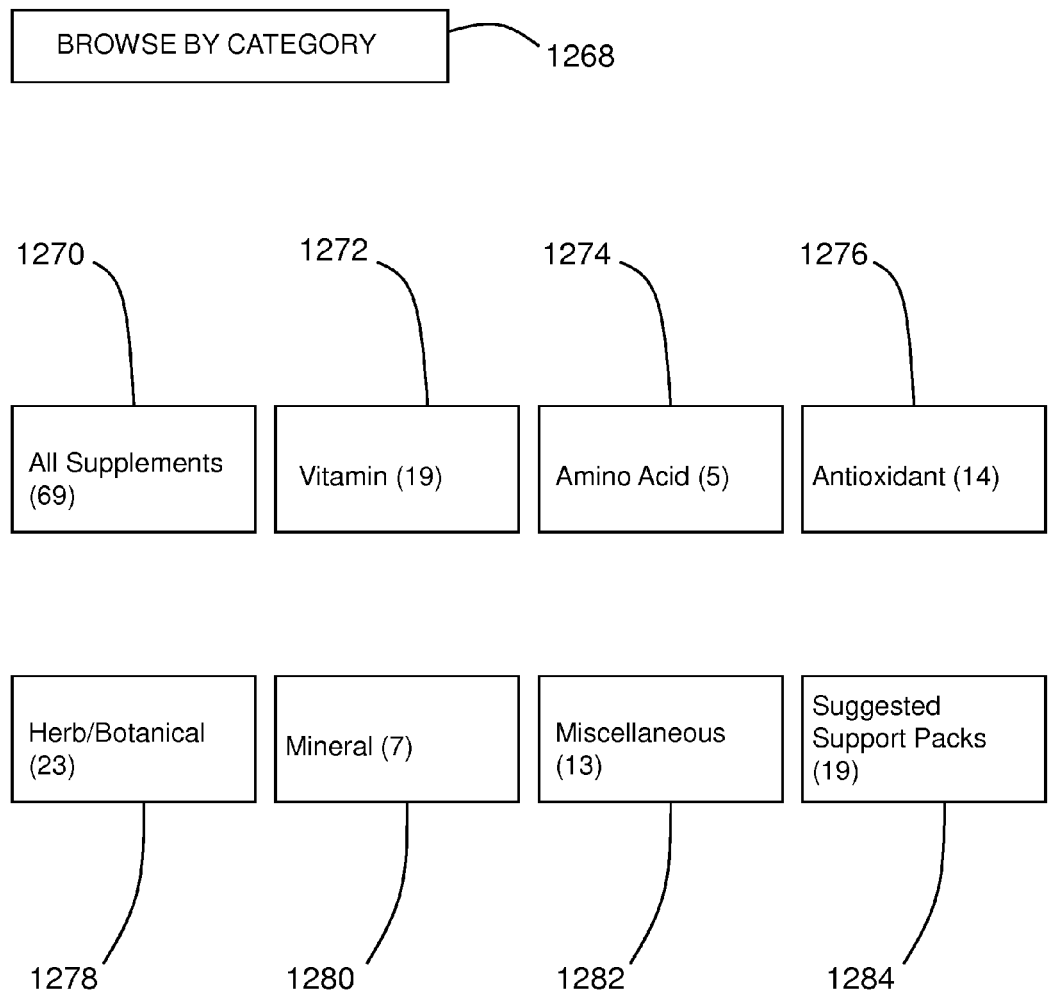
FIG. 19 shows a browse by category user interface.

At this stage of the process, an interface like that depicted in FIG. 19 may be loaded in the user's browser window. The interface may include a heading 1268 directing the user to "browse by category" (or a similar phrase). Alternatively, the user may choose to perform a string search using a text input box (not shown). If the user selects the "browse by category" option, a variety of categories may be presented, depending upon the tablets available for online purchase. In the depicted embodiment, there are categories for "All supplements" 1270, "Vitamin" 1272, "Amino Acid" 1274, "Antioxidant" 1276, "Herb/Botanical" 1278, "Mineral" 1280, "Miscellaneous" 1282, and "Suggested Support Packs" 1284.

Irrespective of the search option selected (i.e., list or string), the process continues at block 1254, where the user selects a medication or group of medications.

Figure 20:
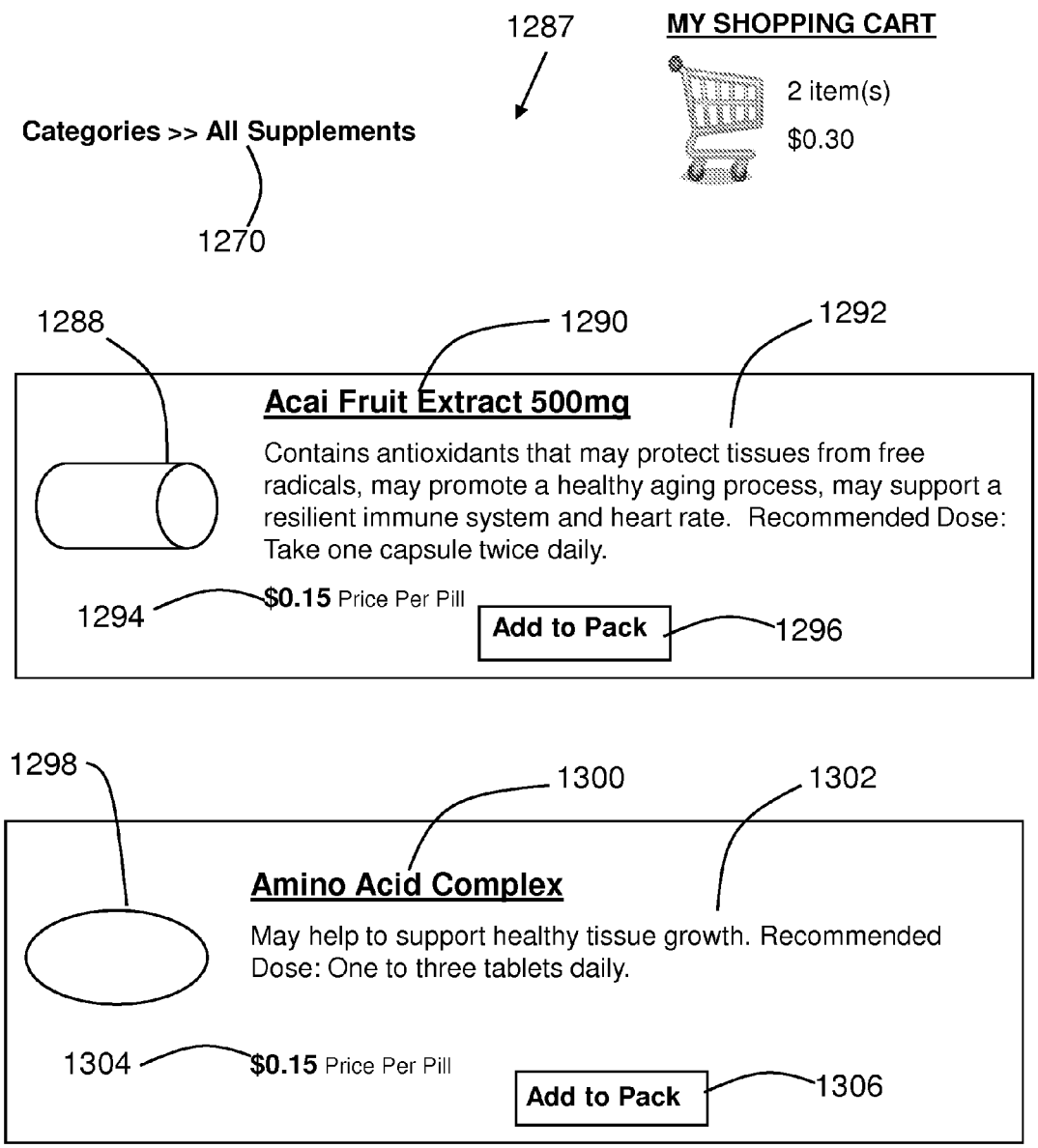
FIG. 20 shows a first ordering interface.
Figure 21:
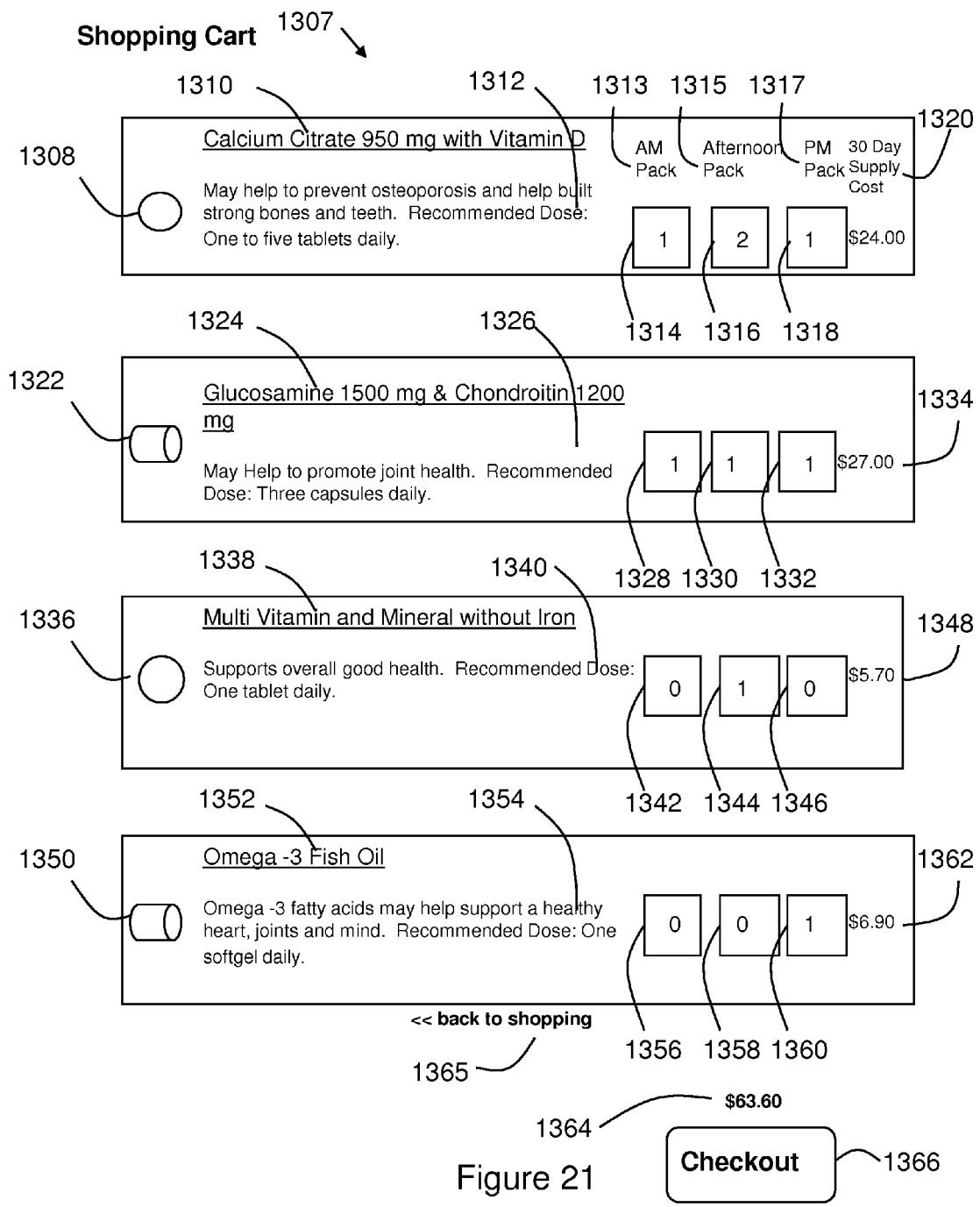
FIG. 21 shows a second ordering interface.

Selecting a medication or group of medications invokes a first ordering interface 1287 like that depicted in FIG. 20. The first ordering interface 1287 comprises information regarding the selected tablet or tablets returned by the search. For instance, in the embodiment depicted in FIG. 20, the user is provided information regarding a list of medications, because the user has chosen to browse by category; i.e., the user has selected the "All Supplements" 1270 list.

The information displayed for the user may comprise an image of the selected medication or medications 1288 and 1298, the name of the medication(s) and the concentration 1290 and 1300, a description of the health benefits, drug interactions, if any, and the recommended dose 1292 and 1302, the price per pill of each medication 1294 and 1304, and a button 1296 and 1306 for adding the desired medication or medications to the user's pack or cart.

Selecting one or more of the "Add to pack" buttons 1296 and 1306 invokes a second ordering interface 1307 (FIG. 21) that includes the user's virtual shopping cart and bringing the user to process step 1256. The second ordering interface 1307 further comprises images of each of the medications 1308, 1322, 1336, 1350 in the user's shopping cart, the name of each medication and a concentration 1310, 1324, 1338, 1352, and a description of the health benefits, the possible side effects, if any, and the recommended dose 1312, 1326, 1340, 1354.

Importantly, the second ordering interface 1307 further comprises a plurality of data input fields, whereby the user may select the quantity of each medication he or she wishes to receive during a particular period—in the depicted embodiment, a 30 day period, but in other embodiments, a 60 or 90 day period. The data input fields additionally permit the user to select a quantity of tablets to be taken in during specified dosing intervals. For example, the user may specify how many of the selected tablets are to be consumed in the AM (i.e., the "AM Pack" 1313), in the afternoon (i.e., the "Afternoon Pack" 1315), and in the PM (i.e., the "PM Pack" 1317) for each day during the particular period. Thus, as illustrated, a user may select a 950 mg Calcium Citrate tablet for consumption once in the AM 1314, twice in the afternoon 1316, and once in the PM 1318. Other dosing configurations may also be selected. If a one-month supply of tablets are ordered, the user will receive 120 Calcium Citrate tablets—one to be taken each morning for the next 30 days, two to be taken in each afternoon, and one to be taken in each evening.

It will be recognized that other dosing intervals may be applied. For example, in some embodiments, the user may specify tablet quantities for more than three daily dosing intervals. The user may be able to specify quantities of tablets by day of the week, or specify tablet quantities for consumption every other day.

In the depicted embodiment, the example user has also chosen to receive a tablet containing 1500 mg Glucosamine and 1200 mg Chondroitin, the tablet to be taken once in the AM 1328, once in the afternoon 1330, and once in the PM 1330 for the next 30 days (totaling 90 tablets at a cost 1334 of $27.00). The user has also selected a single Afternoon dose 1344 of Multi Vitamin and Mineral without Iron; the AM 1342 and PM 1346 data input fields are accordingly filled with zeros, indicating that none of this medication will be placed in the AM and PM packs during the 30 day period. The requested Multi Vitamin tablets will cost the user $5.70 for a 30 day supply 1348. Finally, the user has selected an Omega-3 Fish Oil tablet, also to be taken once a day, but in the evening. Therefore, the AM pack 1356 data input field has an entry of zero, as does the Afternoon Pack data input field 1358; only the PM pack data input field 1360 has a nonzero value; thus, the user will receive the Omega-3 Fish Oil tablet in his PM Pack for the next 30 days. The cost 1362, as shown, for this quantity is $6.90. The prices for each of the plurality of tablets are merely exemplary.

In some embodiments, the user interface may allow the entry of user information, such as the name of the user, address, telephone number, e-mail address, date of birth, height, weight, and sex. The user may also be able to input information about the one or more medical conditions applicable to the user and information about the one or more of the user's physicians. The user may additionally be able to list allergies and current medications.

Furthermore, the user interface may enable the user to select among packaging types for the tablets ordered. For example, the patient may request that each tablet type be packaged individually, or that different tablet types to be consumed at the same time be packaged together. The user may also be able to select packaging options such as type of package, size of package, and child resistant packaging.

After the illustrative user is satisfied that the selected quantity of a particular medication is adequate, the user may choose to continue shopping using the "back to shopping" link 1365 (corresponding to process step 1258). On the other hand, if the user is satisfied with his selection of medications and wishes to finalize his order, he may proceed to checkout using the "Checkout" button 1366 (corresponding to process step 1260). In the depicted embodiment, the user's total 1364 for all medications over the selected period (e.g., 30 days) is displayed as well. At checkout, the user is directed to a third ordering interface, where the user is prompted for billing and shipping information as well as method of payment and payment information. Upon receipt (and in some embodiments, confirmation) of the user's payment, a filling machine in a production facility (which may be a pharmacist's table or desk) generates the required multiple tablet containers/preliminary packages, fills them with the requested multiple tablet orders, and seals and labels each.

Figure 22:
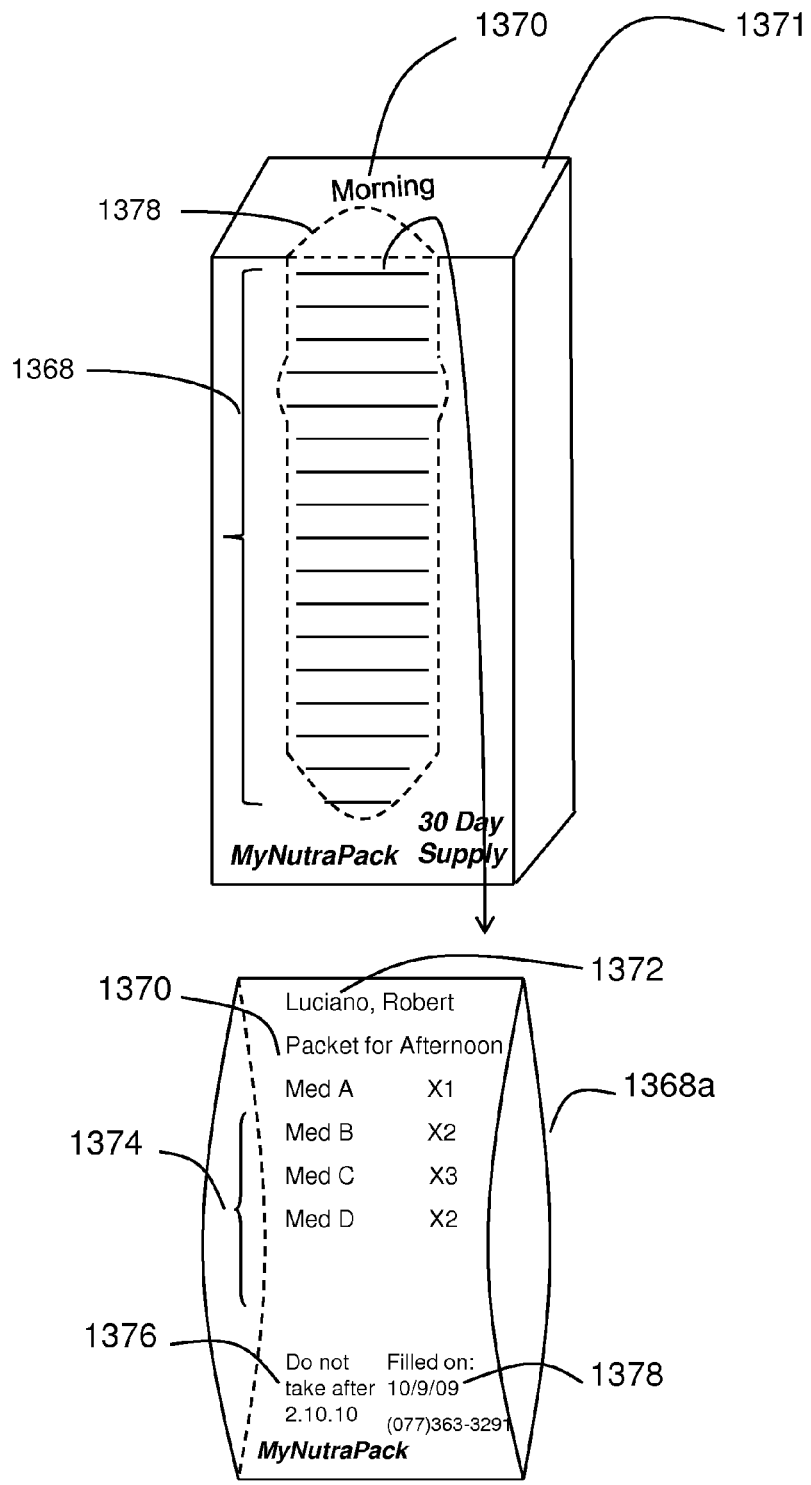
FIG. 22 shows a perspective view of an opened container housing a plurality of pouches.

With regard to the packaging, there is depicted at FIG. 22 an additional embodiment of a secondary container and preliminary packages or pouches. Here, the opened container 1371 is opened along the perforated edge 1378. The result is that the removable face (not shown) is decoupled from the remainder of the container 1371 along the perforated edge 1378.

Within the container 1371 are a plurality of pouches 1368 (30 pouches), e.g., a 30 day supply of medications. As a dosing interval label 1370 printed atop the container 1371 indicates the dosing period for the pouch contents. For example, the label associated with the plurality of pouches 1368 in secondary container 1371 are for consumption during the AM. Note that, although container 1371 holds 30 pouches in the illustrated embodiment, a different number of pouches might be included in the secondary container 1371.

An illustrative preliminary package 1368a is removed from the container 1371. The illustrative pouch 1368a comprises printed text that may include the user's name 1372, the dosing interval 1370, various tablet information 1374 (including the name of each medication within the pouch 1368a as well as the quantity of each medication within the pouch), the expiration date of the medications within the pouch 1376, and a date on which the pouch was filled 1378 with medications.

In the illustrative example, the pouch 1368a is transparent and the medications within the pouch are visible for a variety of reasons including quality control. With reference to the example multiple tablet order provided in the preceding paragraphs, the user would receive 30 individually sealed multiple tablet containers holding the user's AM medications (i.e., 1 Calcium Citrate and 1 Glucosamine/Chondroitin), 30 individually sealed multiple tablet containers holding the user's afternoon medications (i.e., 2 Calcium Citrate, 1 Glucosamine/Chondroitin and 1 Multi-Vitamin and Mineral without Iron), and 30 individually sealed multiple tablet containers holding the user's PM medications (i.e., 1 Calcium Citrate, 1 Glucosamine/Chondroitin and 1 Omega-3 Fish Oil). The AM packs may additionally be packaged in an AM container; the Afternoon packs may be packaged in an Afternoon container, and the PM packs may be packaged in a PM container. The AM, Afternoon, and PM containers may be shipped in a single box.

It is to be understood that the foregoing is a detailed description of illustrative embodiments. The scope of the claims is not limited to these specific embodiments. Various elements, details, execution of any methods, and uses can differ from those just described, or be expanded on or implemented using technologies not yet commercially viable, and yet still be within the inventive concepts of the present disclosure. The scope of the invention is determined by the following claims and their legal equivalents.

What is claimed is:

1. A system for ordering of a plurality of tablets, the system comprising:
   a networked component communicatively coupled to at least one client;
   a user interface disposed on a client that receives at least one prescription input associated with a first plurality of tablets that is different from a second plurality of tablets;
   an ordering application hosted on the networked component and accessible by the client, the ordering application comprising the user interface;
   the user interface displays,
      a first order input associated with a first tablet, the first order input comprising a first daily schedule for consuming the first plurality of tablets, wherein the first daily schedule includes at least one dosing interval selected from a group of dosing intervals consisting of an AM interval, a noon interval, and a PM interval;
      a second order input associated with a second tablet, the second order input comprising a second daily schedule for consumption of the second plurality of tablets, wherein the second daily schedule includes at least one dosing interval selected from the group of dosing intervals consisting of an AM interval, a noon interval and a PM interval;
      an integrated daily schedule that includes the first daily schedule and the second daily schedule;
   wherein the system generates an integrated order after combining the orders from the first order input and the second order input;
   a filling system receives the integrated order and dispenses a first dose from the first plurality of tablets and a second dose from the second plurality of tablets into a plurality of primary containers, in which at least one primary container includes a first tablet and a second tablet;
   a code associated with the primary container, wherein the code associates the tablets in the primary container with the prescription input; and
   a secondary container receives a plurality of primary containers, in which the primary containers further include a combination of different tablets that are consumed at the same time according to the first order input and second order input.

2. The system of claim 1 further comprising a plurality of secondary containers, wherein each secondary container is associated with at least one of the group of dosing intervals consisting of an AM interval, a noon interval and a PM interval.

3. The system of claim 1 wherein each of the plurality of primary containers includes a plurality of pouches, wherein each pouch is associated with a dosing interval indicated in the schedule for consumption.

4. The system of claim 3, wherein the contents of a pouch comprise a first tablet and a second tablet.

5. The system of claim 3 further comprising an integrated label disposed on the secondary container indicating the contents of the pouch.

6. The system of claim 1 further comprising a secondary container, wherein the secondary container houses a plurality of pouches.

7. A online ordering system for a plurality of tablets, the system comprising:
   a networked component communicatively coupled to at least one client;
   a database hosted on the networked server, the database comprising information associated with a plurality of tablet types;
   a user interface disposed on a client that is configured to receive at least one prescription input associated with a first plurality of tablets that is different from a second plurality of tablets;
   an ordering application hosted on the networked component, the ordering application comprising the user interface;
   the user interface configured to display,
      a search parameter and configured to display a subset of data from the database corresponding to the search parameter;
      a first order input associated with a first tablet, the first order input comprising a first daily schedule for consuming the first plurality of tablets, wherein the first daily schedule includes at least one dosing interval selected from a group of dosing intervals consisting of an AM interval, a noon interval and a PM interval;
      a second order input associated with a second tablet, the second order input comprising a second daily schedule for consuming the second plurality of tablets, wherein the second daily schedule includes at least one dosing interval selected from the group of dosing intervals consisting of an AM interval, a noon interval and a PM interval; the user interface further configured to display
an integrated daily schedule that includes the first daily schedule and the second daily schedule;
wherein the system is configured to generate an integrated order that is generated after combining the orders from the first order input and the second order input;
a filling system configured to receive the integrated order and dispense a first dose from the first plurality of tablets and a second dose from the second plurality of tablets into a plurality of primary containers, in which at least one primary container includes a first tablet and a second tablet;
a code associated with the primary container, wherein the code associates the tablets in the primary container with the prescription input; and
a secondary container configured to receive a plurality of primary containers, in which the primary containers further include a combination of different tablets that are consumed at the same time according to the first order input and second order input.

8. The system of claim 7, wherein the subset of data is the result of the application of a filter to the database, the filter comprising a tablet category.

9. The system of claim 7, wherein the user interface is configured to display a plurality of tablet categories, wherein the selection of a tablet category results in the display of all tablet types associated with the selected tablet category.

10. The system of claim 7, wherein the subset of data is the result of the application of a filter to the database, the filter comprising a search string.

11. The system of claim 7, wherein the user interface is configured to display a prompt for a search string, wherein entry of the search string results in the display of all tablets having a tablet type matching the search string.

12. A method for receiving an online ordering for a plurality of tablets, the method comprising:
receiving at least one prescription input at a user interface, wherein the prescription input identifies a first plurality of tablets that is different from a second plurality of tablets;
receiving a first order input with the user interface, the first order input comprising a first daily schedule for consuming the first plurality of tablets, wherein the first daily schedule includes at least one dosing interval selected from a group of dosing intervals consisting of an AM interval, a noon interval and a PM interval;
receiving a second order input with the user interface, the second order input comprising a second daily schedule for consuming the second plurality of tablets, wherein the second daily schedule includes at least one dosing interval selected from the group of dosing intervals consisting of an AM interval, a noon interval and a PM interval;
displaying an integrated daily schedule that includes the first daily schedule and the second daily schedule;
generating an integrated order after combining the orders from the first order input and the second order input;
dispensing, by a filling system, the integrated order, wherein the dispensing by the filling station includes dispensing first dose from the first plurality of tablets and a second dose from the second plurality of tablets into a plurality of primary containers, at least one of the plurality of primary containers including at least one first tablet and at least one second tablet that correspond to the dosing interval;
associating a code with the primary container, wherein the code associates the tablets in the primary container with the prescription input; and
receiving a plurality of primary containers in a secondary container, in which the primary containers are associated with the secondary container that includes a combination of different tablets that are consumed at the same time according to the first order input and second order input.

13. The method of claim 12 further comprising a plurality of secondary containers, wherein each secondary container is associated with at least one of the group of dosing intervals consisting of an AM interval, a noon interval and a PM interval.

14. The method of claim 13, wherein the filling system is communicably coupled to the user interface.

15. The method of claim 14, further comprising transmitting the integrated order to the filling system.

16. The method of claim 15, further comprising dispensing the integrated order into pouches with the filling system, each pouch associated with a dosing interval indicated in the schedule for consumption.

17. The method of claim 16, wherein the plurality of primary containers comprises a plurality of pouches.

18. The method of claim 17, further comprising inserting a plurality of pouches into each secondary container that includes at least two dosing intervals selected from the group of dosing intervals consisting of an AM interval, a noon interval and a PM interval.

19. The method of claim 15, further comprising affixing to the secondary container an integrated label indicating the contents of the pouch.

* * * * *